US011662303B2

(12) United States Patent
Kiger et al.

(10) Patent No.: US 11,662,303 B2
(45) Date of Patent: May 30, 2023

(54) METHOD FOR SPECTRAL STUDY OF A BIOLOGICAL FLUID

(71) Applicants: INSERM (INSTITUT NATIONAL DE LA SANTÉ ET DE LA RECHERCHE MÉDICALE), Paris (FR); UNIVERSITÉ PARIS EST CRÉTEIL VAL DE MARNE, Creteil (FR); ETABLISSEMENT FRANÇAIS DU SANG, La Plaine Saint Denis (FR); ASSISTANCE PUBLIQUE—HOPITAUX DE PARIS, Paris (FR)

(72) Inventors: Laurent Kiger, Paris (FR); Michael Marden, Aulnay sous Bois (FR); Pablo Bartolucci, L'hay les Roses (FR); France Pirenne, Paris (FR)

(73) Assignees: INSTITUT NATIONAL DE LA SANTE ET DE LA RECHERCHE MEDICALE, Paris (FR); UNIVERSITE PARIS EST CRETEIL VAL DE MARNE, Creteil (FR); ETABLISSEMENT FRANCAIS DU SANG; ASSISTANCE PUBLIQUE—HOPITAUX DE PARIS

( * ) Notice: Subject to any disclaimer, the term of this patent is extended or adjusted under 35 U.S.C. 154(b) by 394 days.

(21) Appl. No.: 16/768,366

(22) PCT Filed: Nov. 30, 2018

(86) PCT No.: PCT/EP2018/083173
§ 371 (c)(1),
(2) Date: May 29, 2020

(87) PCT Pub. No.: WO2019/106159
PCT Pub. Date: Jun. 6, 2019

(65) Prior Publication Data
US 2020/0340913 A1    Oct. 29, 2020

(30) Foreign Application Priority Data
Nov. 30, 2017 (FR) ................................... 17 61487

(51) Int. Cl.
*G01N 21/31* (2006.01)
*G01N 33/48* (2006.01)

(52) U.S. Cl.
CPC ............. *G01N 21/31* (2013.01); *G01N 33/48* (2013.01)

(58) Field of Classification Search
CPC ............................... G01N 33/48; G01N 21/31
USPC ............................................. 382/128; 702/19
See application file for complete search history.

(56) References Cited

U.S. PATENT DOCUMENTS

| 6,788,394 | B1 * | 9/2004 | Garcia-Rubio | G01N 21/31 600/314 |
| 6,911,427 | B1 | 6/2005 | Stamler | |
| 8,027,814 | B2 * | 9/2011 | Beyette, Jr. | G01N 21/31 703/2 |
| 9,638,686 | B1 | 5/2017 | Cafferty et al. | |
| 10,088,468 | B2 * | 10/2018 | Cafferty | G01J 3/0291 |
| 2006/0034730 | A1 | 2/2006 | Beyette | |
| 2007/0292963 | A1 | 12/2007 | Dickerson et al. | |
| 2017/0045441 | A1 | 2/2017 | Nciri | |

FOREIGN PATENT DOCUMENTS

EP    1 211 505  A1    6/2002

OTHER PUBLICATIONS

Ascenzi et al: "Heme-based catalytic properties of human serum albumin", Cell Death Discovery, vol. 1, No. 1, Sep. 7, 2015.
Duiser et al: "Iterative model for the calculation of oxyhemoglobin, methemoglobin, and bilirubin in absorbance spectra of cerebrospinal fluid", Clinical Chemistry, p. 338, Feb. 1, 2001.
Kamal et al: "Binding of heme to human serum albumin: steady-state fluorescence, circular dichroism and optical difference spectroscopic studies", Indian Journal of Biochemistry & BIOPHYSICS, pp. 7-12, Feb. 1, 2005.

* cited by examiner

*Primary Examiner* — Ishrat I Sherali
(74) *Attorney, Agent, or Firm* — WCP IP

(57) ABSTRACT

The aim of the present invention is to propose a novel method for spectral study of a biological fluid from an absorption spectrum of a sample of the biological fluid. The inventors have made an original use of spectroscopy in order to accurately determine the protein content of a biological sample, in particular for oxyhaemoglobin, methaemoglobin, bilirubin and the haem bound to serum albumin. Such a method can be used in a variety of applications concerning haem- or haemoprotein- related diseases, in particular diagnostic methods, treatment follow-up methods, methods for determining biomarkers or screening methods. Such a method is also advantageous for qualifying blood bags.

18 Claims, 14 Drawing Sheets

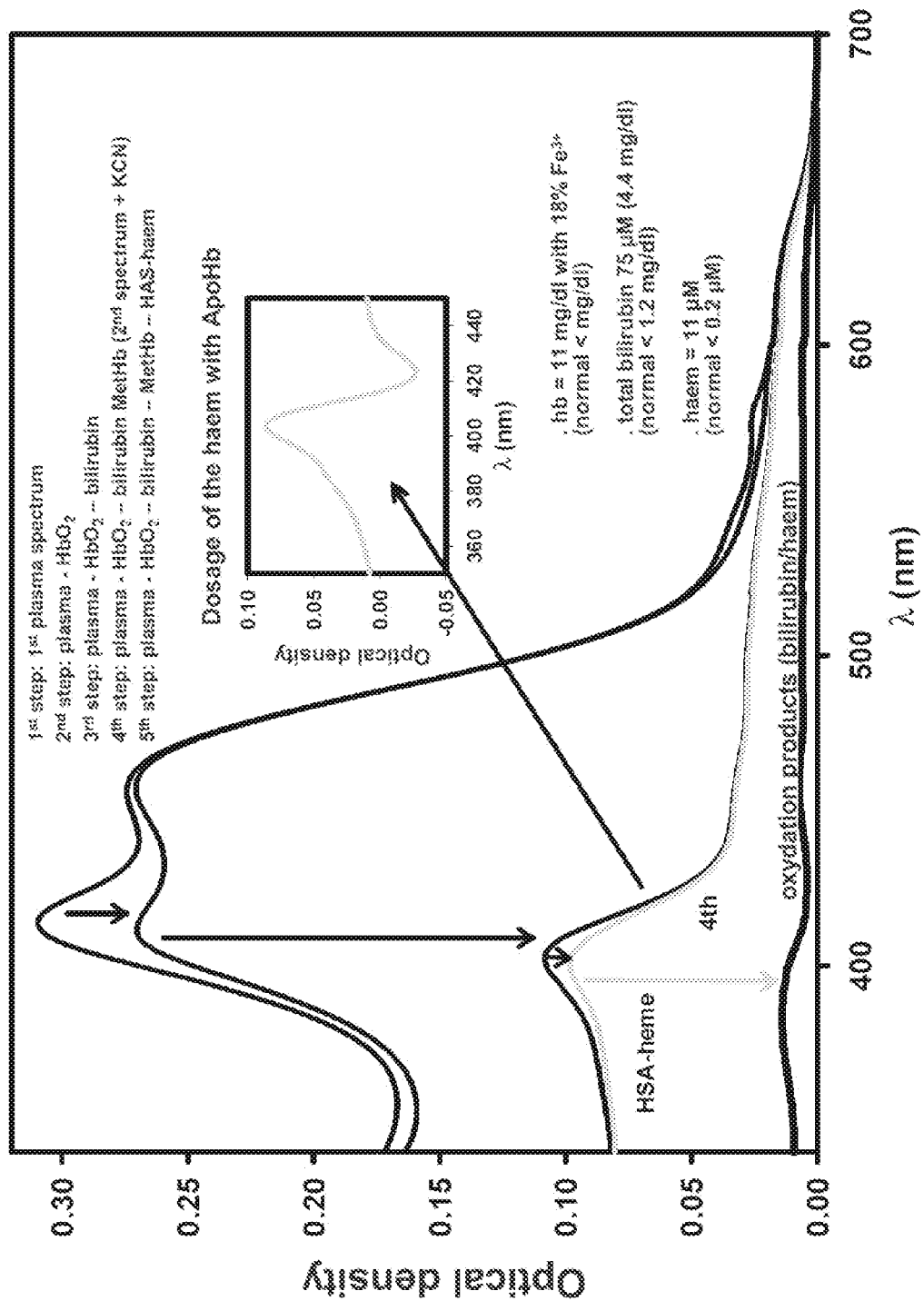

FIGURE 6

| Nomenclature | | Meaning in English |
|---|---|---|
| 1 | SA | Absorbance spectrum |
| 2 | $SA^{KCN}$ | Absorbance spectrum with KCN |
| 3 | SR | Reference spectrum |
| 4 | SC | Calculated spectrum |
| 5 | $SDR^{KCN}$ | Reference differential spectrum with KCN |
| 6 | K | Normalisation coefficient |
| 7 | $d^2$ | Second derivative |
| 8 | $\lambda$ | Wavelength |
| 9 | AS | Serum albumin |
| 10 | HAS | HSA – Human serum albumin |
| 11 | DO | Optical density |
| 12 | DOR | Reference optical density |
| 13 | GR | Red blood cell |

METHOD FOR SPECTRAL STUDY OF A BIOLOGICAL FLUID

TECHNICAL FIELD

The invention relates to a method for the spectral study of a biological fluid starting from an absorption spectrum of a sample of the biological fluid. The invention also relates to the use of spectral data obtained by the spectral study method to determine the content of one or more proteins, in particular haemoproteins as well as the haem and its degradation derivatives. The invention relates to a number of applications in the case of diseases related to the haem and to the haemoprotein. The invention also relates to a computer program comprising instructions for the execution of the steps of a method for spectral study of a biological fluid and a recording medium that is readable by a computer and on which the said program is recorded.

TECHNOLOGICAL BACKGROUND

Haemolytic diseases including sickle cell anaemia, thalassaemia, membrane pathologies of the red blood cell, enzyme deficits (glucose 6-phosphate dehydrogenase or G6PD), autoimmune haemolytic anaemia (AIHA), paroxysmal nocturnal haemoglobinuria, some infections (malaria), atypical haemolytic uremic syndrome, and also delayed haemolytic transfusion reactions (DHTR) or related to a prosthetic heart valve dysfunction, or haemolysis during circulating endothelial cell or extracorporeal membrane oxygenation circulation (CEC or ECMO), after the lysis of red blood cell in the blood compartment lead to an increase in plasma haemoglobin and the haem in oxidized form not protected by globin also called haemin which transiently binds to serum albumin (AS) and almost irreversibly to haemopexin (Hx). The presence of haem may also be considered in haemolysis of the newborn due to their low plasma concentration of haptoglobin that is responsible for the clearance of plasma haemoglobin, as well as monitoring of the treatment of porphyrias by intravenous injection of haem solution.

Other pathologies may be mentioned such as diabetes, spesis and other inflammatory syndromes, amyloidosis, neurodegenerative diseases (Alzheimer, Huntington . . . ), muscular diseases (release of myoglobin), myopathies.

In addition, the measurement of haemoglobin and, in particular, of the cytotoxic haem at high concentrations compared to homeostasis in the cell as well as in an extra-cellular medium (biological fluids) or in abnormal molecular and cellular aggregates (atheroma deposits or senile plaques), remains an important biological parameter for the diagnosis of many pathologies.

The plasma haem and haemoglobin activate a cascade of reactions.

The plasma haem and haemoglobin generate pro-inflammatory reactions possibly via macrophages and endothelial cells, for example by binding to the TLR4 receptor: this induces inter alia the expression of cytokines and of the pro-aggregating tissue factor and, finally, the adhesion of leukocytes and red blood cells to the vascular walls. The haem also activates the complement by the alternate route.

The plasma haem and haemoglobin also have the effect of activating pro-coagulant reactions by facilitating the formation of the thrombus and/or pro-oxidant reactions by generating reactive oxygen species (ROS or free radicals) or reactive nitrogen species (RNS) via the Fenton reaction, and participating in the oxidation of membrane lipids.

In addition, plasma haem and haemoglobin are responsible for apoptosis and tissue necrosis of the endothelium but also of the organs.

In addition, the plasma haem and haemoglobin act in the presence of chronic high vascular tone or even induce changes in the cardiovascular anatomy. The plasma haemoglobin has a vasoconstrictor effect by eliminating the nitric oxide produced by endothelial NO synthase via its dioxygenase function ($HbFe_2$ in reaction with $O_2$ and NO gives $HbFe^{3+}$ and $NO^{3-}$). The haem induces a vasodilating effect via its degradation by the endothelial haem oxygenase. In fact, the carbon monoxide produced by the haem catabolism reaction may inhibit the NO dioxygenase activity of endothelial globins and thus potentiate the NO/cGMP/PKG pathway (pathway for modulating vascular tone by production of NO in the endothelial cells inducing the production of cGMP by guanylate cyclase, then the activation of protein kinase C in smooth muscle cells and ultimately vasodilation). Such a biochemical reaction depends on the haem oxygenase activity which, although overexpressed by the haem, may be insufficient to catabolize an excess of the haem generating reactive oxygen species (ROS), or even alteration of the cell membrane and ultimately vasoconstriction and local inflammation.

Haptoglobin (Hp) and haemopexin (Hx) are two proteins of the acute phase of inflammation which play a major role in the elimination of plasma haemoglobin and haem respectively by endocytosis in the reticulo-endothelial system and macrophages/hepatocytes respectively. In the case of chronic intravascular haemolysis, or following a severe haemolytic crisis, the concentration of these two proteins decreases until it is almost depleted. The haem, as well as the haemoglobin, may then exert toxic effects by extravasation through the wall of the vessels, accumulation on the surface of the endothelium by reaction with the NO produced by the NO synthase causing local vasoconstriction and participating in significant organ damage (kidney, liver, spleen, heart, brain, lungs). The activity of the haem oxygenase is therefore crucial to ensuring the catabolism of the haem, and thus to limiting the cytotoxic reactions linked to haemoglobin/haem.

While the plasma haemoglobin assay is accessible by spectroscopy and is often correlated with haemolysis markers such as lactate dehydrogenase (LDH) and haptoglobin (these latter haemolysis markers are not always reliable), that of haem is technically difficult to effect due to the presence of a generally higher concentration of bilirubin and haemoglobin in the plasma, which hinders the detection of haem. Very few reliable data in the literature are reported and often the plasma haem refers to haemoglobin. In addition to this observation, its measurement remains a major issue in the assessment of the post-haemolysis risks of patients in haemolytic crisis. Its presence is closely related to the depletion of haptoglobin and haemopexin, but also to an oxidation reaction of haemoglobin which leads to the production of methaemoglobin (metHb) then to the dissociation of globin and haem which then becomes free. The presence of plasma haem also reveals the presence of membrane debris, microparticles and other red blood cell ghosts due to haemolysis which may be involved in pathological reactions. Degradation of the haem outside of the haem oxygenase management will result in the release of iron. This transition metal alters cellular structures via oxidation reactions with $O_2$ (ROS) and phospholipids, in particular, if the iron storage and transfer proteins are absent. The degradation of haem in the vascular compartment will therefore be a component of toxic free serum iron not complexed with haem (plasma and globin) as long as the transferrin coefficient is high; iron may also be linked to the haem through extravasation before being released into the tissues.

Finally, it should be noted that a component of plasma haem may reflect dyserythropoiesis with the accumulation of haem in the marrow induced by excessive haemolysis and by iron overload in the body (too much intestinal incorporation).

Due to the significant toxicity of free haem in plasma and/or haem related to serum albumin (serum albumin/haem) via oxidation reactions with reactive oxygen species (ROS), reactive nitrogen oxide species (RNOS), and the many molecules interacting with serum albumin (AS), their almost certain presence in many pathological situations and the current absence of a reliable measurement method, there is a significant need to develop an easy method to implement a spectral study of blood plasma which may be used to determine the total haem content in the blood plasma which comprises haemoglobin, plasma haem and all other abnormally present forms forming a complex with the haem. The degradation/oxidation products of the haem are important biomarkers of intra-tissue and intravascular haemolysis and of hepatic or even endothelial or placental metabolism in the context of preeclampsia.

Unconjugated and conjugated bilirubin are two important plasma pigments. Although the conjugated form is more soluble, bilirubin would have a protective antioxidant and antihypertensive role except in the case of hyperbilirubinemia (severe jaundice when bilirubin is greater than the binding capacity of serum albumin with, for example, brain damage); this is why the inventors also developed the spectral measurement. The measurements initially developed on blood plasma may be applied to other samples and biological fluids such as: urine (in which it is possible to demonstrate haematuria/haemoglobinuria and/or renal and hepatic damage, as well as bilirubin degradation derivatives after oxidation such as urobilin and stercobilin), interstitial fluids (in which ascites may be detected in the presence of haemolysis), amniotic fluid (in which it is possible to highlight haemolytic anaemias as the degradation products of haemoglobin during preeclampsia), lymph, cerebrospinal fluid but also in biological samples for transfusion purposes, such as blood or its derivatives such as blood plasma (labile blood products), cell culture.

SUMMARY OF THE INVENTION

The present invention aims to propose a new method for the spectral study of a biological fluid from an absorption spectrum of a sample of the biological fluid.

A method is therefore proposed for the spectral study of a biological fluid comprising the steps of:
  a) obtaining an absorption spectrum of a sample of the biological fluid;
  b) subtraction from said absorption spectrum of a spectral component associated with oxyhaemoglobin ($HbO_2$) in order to obtain an intermediate calculated spectrum SC1;
  c) subtraction from said intermediate calculated spectrum SC1 of a spectral component associated with methaemoglobin (metHb) in order to obtain an intermediate calculated spectrum SC2;
  d) subtraction from said intermediate calculated spectrum SC2 of a spectral component associated with bilirubin in order to obtain an intermediate calculated spectrum SC3;
  e) subtraction from said intermediate calculated spectrum SC3 of a spectral component associated with the haem linked to serum albumin in order to obtain an intermediate calculated spectrum SC4; and optionally subtraction from said intermediate calculated spectrum SC4 of a spectral component associated with one or more other proteins and/or biological molecules present in the biological fluid.

For example, another protein may be the haem linked to haemopexin.

Alternatively, in the absence of rare and atypical spectral forms, it is possible to simulate the SC3 spectrum in step e) as a linear combination of the reference spectra associated with the serum albumin/haem and the haemopexin/haem.

It is also proposed to use the spectral data obtained by the previous method to determine the content of one or more proteins present in a biological fluid chosen from $HbO_2$, MetHb, bilirubin, serum albumin/haem, haemopexin/haem, carboxylated haemoglobin (HbCO), a biomarker of haem catabolism by haem oxygenase, myoglobin, porphyrins, degradation products of bilirubin such as bilirubin degradation products by serum albumin/haem in the presence of reactive oxygen species ($H_2O_2$) (mono-pyrrole isomers (haem-BOXes), di-pyrroles (PDPs) and biliverdin), and porphobilin, stercobilin and urobilin in the urine.

The use of spectral data obtained by the previous method makes it possible to consider determining the content of other biological pigments in the event of disruption of the function of an organ or other visceral damage resulting, for example, in cytolysis. Finally, the quantification or pharmacokinetics of a drug or diagnostic molecule (or degradation products) is also made available by studying the spectral properties obtained after the subtraction of the other components conventionally present in the plasma.

The present description also describes a computer program comprising instructions for the execution of the steps of a method for spectral study of a biological fluid according to the invention, or of a method of use according to the invention when said program is executed by a computer.

It should be noted that the computer programs mentioned in this presentation may use any programming language, and may be in the form of source code, object code, or intermediate code between source code and object code, such as in a partially compiled form, or in any other desirable form.

The description also relates to a computer-readable recording medium on which a computer program is recorded comprising instructions for the execution of steps of a method for spectral study of a biological fluid such as previously described, or a method of use as previously described.

The recording (or information) media mentioned in this presentation may be any entity or device capable of storing the program. For example, the support may include a storage means, such as a ROM, for example a CD-ROM or a microelectronic circuit ROM, or else a magnetic recording means, for example a floppy disc or a hard disc.

On the other hand, the recording media may correspond to a transmissible medium such as an electrical or optical signal, which may be routed via an electrical or optical cable, by radio or by other means. The program according to the invention may, in particular, be downloaded from a network of the Internet type.

Alternatively, the recording media may correspond to an integrated circuit incorporating the program, wherein the circuit is adapted to execute, or to be used in the execution of, the method in question.

The following is also proposed:
method for determining the content of at least one protein present in a biological fluid, wherein the determination method comprises:
  implementing the study method as previously described,
  obtaining an oxyhaemoglobin content from the absorption spectrum,
  obtaining a methaemoglobin content from the intermediate calculated spectrum SC1,
  obtaining a bilirubin content from the intermediate calculated spectrum SC2, and
  obtaining a haem content linked to serum albumin from the intermediate calculated spectrum SC3 and/or haem linked to haemopexin.
method for predicting that a subject is at risk of suffering from a disease related to the haem or to a haemoprotein, wherein the method of prediction comprises at least the steps consisting of:
  performing the steps of a method for determining at least one protein content in a biological sample of the subject, so as to obtain determined parameters, wherein the determination method is as previously described, and
  predicting that the subject is at risk of suffering from a disease related to the haem (degradation products) or to a haemoprotein on the basis of the determined parameters.
method for diagnosing a disease related to the haem or a haemoprotein, wherein the diagnostic method comprises at least the steps consisting of:
  performing the steps of a method for determining at least one protein content in a biological sample of the subject, so as to obtain determined protein contents, wherein the determination method is as described above, and
  diagnosing the disease related to the haem or to a haemoprotein on the basis of the determined protein contents.
method for defining the stages of a disease related to the haem or a haemoprotein, wherein the definition method comprises at least the steps consisting of:
  performing the steps of a method for determining at least one protein content in a biological sample of the subject, so as to obtain determined protein contents, wherein the determination method is as described previously, and
  defining the stages of the disease related to the haem or to a haemoprotein on the basis of the determined protein contents.
method for identifying a therapeutic target for preventing and/or treating a disease related to the haem or to a haemoprotein, wherein the method comprises at least the steps consisting of:
  performing the steps of a method for determining at least one protein content in a biological sample of images of a first subject, so as to obtain a first determined protein content, wherein the determination method is as previously described and the first subject is a subject suffering from a disease related to the haem or to a haemoprotein,
  performing the steps of the method for determining at least one protein content in a biological sample of a second subject, so as to obtain a second determined protein content, wherein the method of determination is as previously described and the second subject is a subject not suffering from a disease related to the haem or to a haemoprotein,
  selecting a therapeutic target based on the comparison of the first and second determined protein contents.
method for identifying a biomarker, wherein the biomarker is a diagnostic biomarker of a disease related to the haem or to a haemoprotein, a biomarker of susceptibility to a disease related to the haem or to a haemoprotein, a prognostic biomarker of a disease related to the haem or haemoprotein, or a predictive biomarker in response to treatment of a disease related to the haem or a haemoprotein, wherein the method comprises at least the steps consisting of:
  implementing the steps of a method for determining at least one protein content in a biological sample from a first subject, so as to obtain a first determined content, wherein the determination method is as previously described and the first subject is a subject suffering from a disease related to the haem or a haemoprotein,
  performing the steps of the method for determining at least one protein content in a biological sample of images of a second subject, so as to obtain a second determined protein content, wherein the determination method is as previously described and the second subject is a subject not suffering from a disease related to the haem or haemoprotein, and
  selecting a biomarker on the basis of the comparison of the first and second determined protein contents.
method for screening a compound that is useful as a drug, wherein the compound has an effect on a known therapeutic target for preventing and/or treating a disease related to the haem or to a haemoprotein, wherein the method comprises at least the steps consisting of:
  implementing the steps of a method for determining at least one protein content in a biological sample of a first subject, so as to obtain a first determined protein content, wherein the determination method is as previously described and the first subject is a subject suffering from the disease related to the haem or a haemoprotein and having received the compound,
  performing the steps of a method for determining at least one protein content in a biological sample of a second subject, so as to obtain a second determined protein content, wherein the determination method is as previously described and the second subject is a subject suffering from a disease related to the haem or a haemoprotein, and who has not received the compound, and
  selecting a compound on the basis of the comparison of the first and second determined protein contents.
method for qualifying or disqualifying medical bags containing a biological sample of the subject, wherein the method comprises at least the steps consisting of:
  performing the steps of a method for determining at least one protein content in the medical bag, so as to obtain determined protein contents, wherein the determination method is as previously described, and
  qualifying or disqualifying medical bags on the basis of determined protein contents.
method for monitoring a treatment against a disease related to the haem or to a haemoprotein in a subject suffering from the disease related to the haem or to a haemoprotein, and who has received the treatment, wherein the method comprises at least the following steps:

performing the steps of a method for determining at least one protein content in a biological sample of the subject, so as to obtain determined protein contents, wherein the determination method is as previously described, and monitoring the determined protein content to follow a treatment against a disease related to the haem or to a haemoprotein in a subject suffering from the disease related to the haem or to a haemoprotein, and who has received the treatment.

BRIEF DESCRIPTION OF THE DRAWINGS

FIG. 1: Method for assaying $HbO_2$, metHb, plasma haem and haem degradation and oxidation products by a UV/visible spectrophotometric approach on a plasma sample from a patient with sickle cell anaemia after iatrogenic post-transfusion haemolysis (DHTR).

FIG. 6: abbreviations used in the patent application.

DETAILED DESCRIPTION OF THE INVENTION

Definitions

Figure 2A:
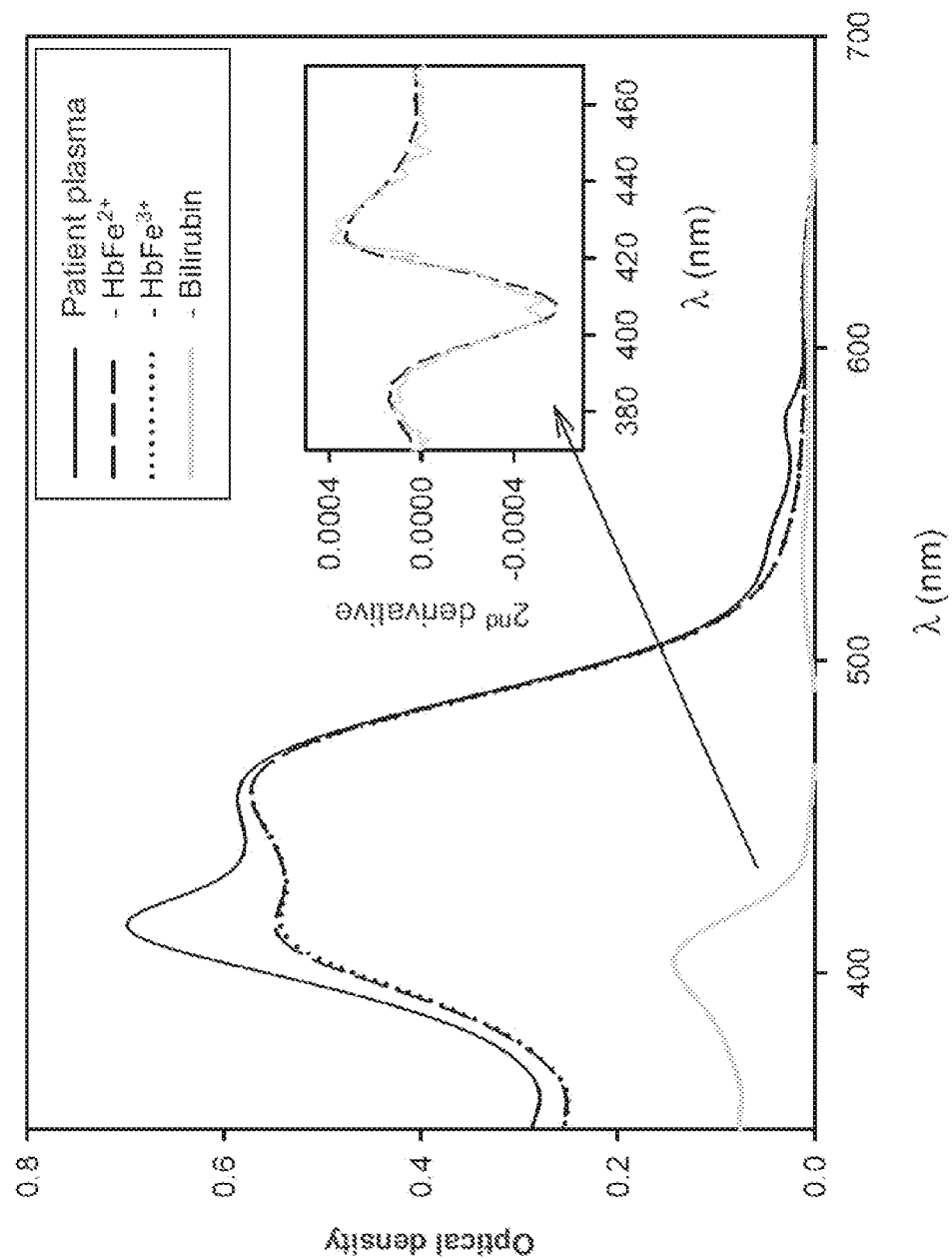
FIG. 2a: Method for assaying haemoglobin $Fe^{2+}O_2$ and $Fe^{3+}$, plasma haem and haem degradation and oxidation products by a UV/visible spectrophotometric approach on a plasma sample from a patient with sickle cell anaemia and a mechanical heart valve problem.

Within the meaning of the invention, the term "absorption spectrum" must be taken in its first sense, i.e. a spectrum obtained by the passage of an electromagnetic wave, in particular of light, through a transparent or semi-transparent medium, in which the absorption weakens (or even eliminates) the contributions of certain frequencies, which gives characteristic curves of said medium. In the context of the invention, the absorption spectrum makes it possible to determine the concentration of different substances present in the biological fluid by measuring the intensity of the electromagnetic radiation which it absorbs at different wavelengths. The absorption spectrum may be easily obtained by using apparatuses well known to those skilled in the art, generally by using a spectrometer, for example a computer-controlled spectrometer.

Within the meaning of the invention, the term "spectral component" corresponds to a component of the absorption spectrum. In the context of the invention, a spectral component is associated with one or more substances present in the biological fluid.

Within the meaning of the invention, the term "biological fluid" corresponds to a fluid capable of containing haemolysis. The biological sample may be chosen from among urine, interstitial fluids, amniotic fluid, blood, and blood derivatives such as, for example, blood plasma. In a particular embodiment, the biological fluid is blood plasma.

Within the meaning of the invention, the term "content" must be taken in its primary sense, i.e. the quantity of the entity of interest. The content may be expressed in mass content, for example in picogram (pg) or in molarity, for example in micromoles (μM). Preferably, within the meaning of the invention, the content is a mass concentration expressed in μmol/l or in μM, preferably the mass concentration is expressed in pg/l, preferably the dosages of serum proteins according to the invention are generally expressed in micromoles (μM), in milligrams per deciliter (mg/dl) or in grams per litre (g/l).

The term "oxyhaemoglobin" or "$HbO_2$" corresponds to the oxygenated form of haemoglobin, i.e. haemoglobin whose reduced haem ($Fe^{2+}$) is linked to oxygen.

Methaemoglobin (metHb) is a form of haemoglobin in which haem iron is in the +3 oxidation state ($Fe^{3+}$) and which does not bind the diatomic ligands of $Fe^{2+}$ such as $O_2$, CO or NO; conversely $Fe^{3+}$ binds strongly to $CN^-$ and $N_{3-}$ anions, but weakly to $H_2O$ and $OH^-$.

Bilirubin is a degradation product of haemoglobin. It generally circulates in the blood linked to albumin.

The haem linked to serum albumin is oxidized ($Fe^{3+}$) and may be involved in enzymatic catalysis reactions.

The haem linked to haemopexin is oxidized ($Fe^{3+}$) and is not involved in enzymatic catalysis reactions due to the very strong hexa-coordination of iron (His-Fe-His). Unlike metHb, ferric ligands bind to serum albumin/haem and haemopexin/haem with low affinity.

The "reference spectra" or "SR" are absorption spectra obtained for a single protein, as explained below. The reference spectra are generally obtained before the implementation of the method according to the invention.

The "calculated spectra" or "intermediate calculated spectra" or "SC" are spectra obtained after subtraction from the measured absorption spectrum of a spectral species from its reference spectrum weighted by a normalization factor "K", the ratio between the amplitude of the signal of the determined species and its reference; each step of the protocol below corresponds to a new spectrum that is calculated as the sequential determination of the contribution of each spectral species and their subtraction from the initial absorbance spectrum.

Method for Spectral Study of Biological Fluid

The inventors have highlighted a spectral study method that is particularly suitable for analyzing the various components of a biological fluid. This method may be used, in particular, to determine the content of one or more proteins present in the biological fluid.

Thus, a method of spectral study of a biological fluid is described, comprising the steps of:
  a) obtaining an absorption spectrum of a sample of the biological fluid;
  b) subtracting from said absorption spectrum of a spectral component associated with oxyhaemoglobin ($HbO_2$) in order to obtain an intermediate calculated spectrum SC1;

c) subtracting from said intermediate calculated spectrum SC1 of a spectral component associated with methaemoglobin (metHb), in order to obtain an intermediate calculated spectrum SC2;

d) subtracting from said intermediate calculated spectrum SC2 of a spectral component associated with bilirubin in order to obtain an intermediate calculated spectrum SC3;

e) subtracting from said intermediate calculated spectrum SC3 of a spectral component associated with the haem linked to serum albumin, in order to obtain an intermediate calculated spectrum SC4; and, possibly, f) subtracting from said intermediate calculated spectrum SC4 of a spectral component associated with one or more other proteins and/or biological molecules present in the biological fluid, in order to obtain an intermediate calculated spectrum SCS. Another protein present in plasma may be haemopexin/haem, especially in cases of haemolysis.

Those skilled in the art will know how to adapt the order of the different steps in the case of an atypical biological sample by following the decreasing order of the intensity of the signals to be measured on the same domain of the light spectrum and for two signals of the same intensity by nonlinear simulations of the entire signal from their second reference derivatives. The analysis may be carried out for a species with low intensity in comparison with the whole of the species of the measured absorbance spectrum if there exists a domain of the light spectrum which is specific or quasi-specific to it, for example about 577 nm for $HbO_2$.

Step a)

Step a) consists in obtaining an absorption spectrum of a sample of the biological fluid.

As used hereinafter and in all aspects of the invention, the term "sample" means blood, fresh whole blood, peripheral blood, peripheral blood mononuclear cells (PBMC), serum, plasma or urine.

Obtaining an absorption spectrum may be effected by methods that are well known to those skilled in the art, for example with a spectrometer, preferably a computer-controlled spectrometer. The biological fluid sample may be analyzed immediately after collection or at a later time. For example after storage at a temperature between 10° C. and 5° C. for several hours. The sample may also be frozen and then stored, for example at a temperature from −20° C. to −80° C. Freezing allows easy storage and subsequent analysis while limiting as far as possible the risk of alteration of the proteins and/or biological molecules in the sample assayed. The sample may also be stored with an agent that stabilizes the protein(s). The preparation of the sample is part of the routine work of those skilled in the art in order to obtain the absorption spectrum of the sample of the biological fluid. For example, the sample may also be prepared in such a way as to increase the detectability of the protein(s), for example by fractionating, diluting and/or concentrating the sample.

In a particular embodiment, the spectrum of step a) is obtained from a sample of the diluted biological fluid, so as to obtain a maximum optical density (DO) less than or equal to 2, preferably less than or equal to 1. This means, an optical density of the absorption spectrum of the sample of the biological fluid whose maximum value is less than or equal to 2, preferably less than or equal to 1.

In a particular embodiment, the spectrum of step a) is obtained in a range of wavelengths comprising all or part of the ultra-violet and all or part of the visible, preferably in a range of wavelengths ranging from about 200 nm to about 1000 nm, preferably ranging from about 300 nm to about 700 nm.

Advantageously, the sample of the biological fluid is buffered at a pH of less than 8, preferably between 7.35 and 7.45, more preferably equal to 7.4 (physiological value), since the spectrum of the metHb form depends on the pH with a pKa ($H_2O \rightarrow OH^-$) close to 8. The sample may be buffered with a buffer solution, for example a buffer solution chosen from among potassium phosphate, 50 mM sodium phosphate, 50 mM NaCl pH 7.4.

Step b)

Step b) consists in subtracting from said absorption spectrum of a spectral component associated with oxyhaemoglobin ($HbO_2$) in order to obtain an intermediate calculated spectrum SC1.

In a particular embodiment, step b) is carried out by subtracting the spectral component associated with $HbO_2$ that is obtained by normalization of a reference spectrum SR1 of $HbO_2$, said normalization being carried out with respect to said absorption spectrum by calculating a normalization coefficient K1 at a wavelength of about 416 nm, about 543 nm or about 577 nm, preferably about 577 nm.

By "reference spectrum SR1 of $HbO_2$" is meant an absorption spectrum of a sample of $HbO_2$, i.e. a sample comprising only, or almost only, $HbO_2$. Samples comprising only, or almost only, $HbO_2$ may be obtained from red blood cells of a healthy non-smoking subject, washed in physiological saline and, after lysis, in a 5-10 mM phosphate buffer at pH 7.4, and then centrifuged at 15,000 g to recover the $HbO_2$ in the supernatant, which may then be purified on a size exclusion and/or ion exchange chromatographic column.

Advantageously, the sample comprising only, or almost only, $HbO_2$ as protein is buffered at a pH of less than 8, preferably between 7.35 and 7.45, more preferably equal to 7.4, and preferably at a pH identical to the pH of the biological fluid sample.

Advantageously, the normalization coefficient K1 is calculated by determining the ratio between the values of the second derivatives of the absorption spectrum and of the reference spectrum SR1 at a wavelength of about 416 nm, about 540 nm, or about 577 nm, preferably about 577 nm.

The term "about", is understood to mean that the wavelength is approximately equal to the value X when the wavelength is greater than or equal to X−1 nm and less than or equal to X+1 nm.

Thus, SC1 may be obtained in the following way at a wavelength I of about 416 nm, about 543 nm, or about 577 nm, preferably about 577 nm:

$$SC1 = SA - K1 \times SR1$$

where:

SR1 designates the reference spectrum of $HbO_2$;

K1 is given by the following expression:

$$K1 = \left(\frac{d^2 SA}{d\lambda^2}\right) \bigg/ \left(\frac{d^2 SR1}{d\lambda^2}\right)$$

where $$\left(\frac{d^2 SA}{d\lambda^2}\right)$$

is the second derivative of the absorption spectrum SA at a given
wavelength λ, while $$\left(\frac{d^2 SR1}{d\lambda^2}\right)$$

is the second derivative of the reference spectrum of $HbO_2$

Generally, the normalization coefficient K1 takes into account the dilution factor of the biological fluid.

$HbO_2$ is the oxyhaemoglobin A ($HbAO_2$), the oxyhaemoglobin F ($HbFO_2$), the oxyhaemoglobin A2 ($HbA2O_2$) and the glycated forms. In general, $HbO_2$ is $HbAO_2$ in adults, while $HbO_2$ is a mixture of $HbAO_2$ and $HbFO_2$ in newborns or in patients with the most common variants of Hb S, C, E.

Step c)

Step c) consists in subtracting from said intermediate calculated spectrum SC1 of a spectral component associated with methaemoglobin (metHb) in order to obtain an intermediate calculated spectrum SC2.

Advantageously, the spectral component associated with methaemoglobin (metHb) is obtained from:
sample absorption spectrum (SA),
absorption spectrum of the sample treated with KCN ($SA^{KCN}$),
reference spectrum of metHb (SR2), and
reference spectrum of metHb SR2 treated with KCN.

The differential spectrum SD equal to $SA-SA^{KCN}$, hereinafter $SD^{KCN}$ is obtained by subtraction of the data of DO $SA-SA^{KCN}$ corresponding to the same wavelengths, preferably by subtraction: $DO_{max}-DO_{min}$.

Advantageously, the normalization coefficient K2 is calculated by determining the $SD^{KCN}$ ratio with a reference differential spectrum $SDR^{KCN}$ obtained from a sample comprising only, or almost only, metHb in the absence of KCN vs being saturated in KCN.

Thus, SC2 may be calculated as follows:

$$SC2 = SC1 - K2 \times SR2$$

where:
SR2 is the metHb reference spectrum (obtained from a sample comprising only, or almost only, metHb in the absence of KCN), and
In addition:

$$K2 = \frac{SD^{KCN}}{SDR^{KCN}} = \frac{DO\max - DO\min}{DO^R\max - DO^R\min}$$

Generally, $DO_{max}$ and $DO^R_{max}$ (reference optical density) are at a wavelength of about 404 nm, while $DO_{min}$, and $DO^R_{min}$ are at a wavelength of about 424 nm, or vice versa.

Advantageously, in order to have the highest signal amplitude and thus increase the sensitivity for the metHb assay by adding KCN, and also in order to eliminate a spurious signal originating from a displacement of the baseline or a diffusional component, K2 is calculated by taking the absolute value of the difference between the maximum DO ($DO_{max}$) and the minimum DO ($DO_{min}$) of the $SD^{KCN}$ spectrum, generally at about 404 nm and about 424 nm.

In a particular embodiment, the metHb content may be assayed by analyzing the second derivative of $SD^{KCN}$ by taking the difference in the derivative values between about 404 nm and about 424 nm, or by directly analyzing the value of the second derivative at one of these wavelengths.

Alternatively, SC2 may be calculated as follows:

$$SC2 = SC1 - KSD2 \times SR2$$

with $$KSD2 = \left[\left(\frac{d^2 SD^{KCN}}{d\lambda^2}\right)_{\lambda=406} - \left(\frac{d^2 SD^{KCN}}{d\lambda^2}\right)_{\lambda=421}\right] / \left[\left(\frac{d^2 SDR^{KCN}}{d\lambda^2}\right)_{\lambda=406} - \left(\frac{d^2 SDR^{KCN}}{d\lambda^2}\right)_{\lambda=421}\right]$$

al spectrum re

By "differential spectrum $SD^{KCN}$" or "spectrum $SD^{KCN}$" or "$SD^{KCN}$", is meant a differential spectrum representing the spectral difference in optical density (DO) before and after addition of KCN.

By "$SDR^{KCN}$ differential spectrum" or "$SDR^{KCN}$ spectrum" or "$SDR^{KCN}$" is meant a reference differential spectrum representing the spectral difference in optical density before and after addition of KCN for a reference spectrum of metHb (SR2).

By "metHb reference spectrum" or "SR2" is meant an absorption spectrum of a metHb sample, i.e. a sample comprising only, or almost only, metHb. Such a sample may be obtained commercially or by the implementation of biochemical protocols and conventional purification methods. Advantageously, the sample comprising only, or almost only, metHb as protein, and is buffered at a pH of less than 8, preferably between 7.35 and 7.45, more preferably equal to 7.4, and preferably at a pH identical to the pH of the biological fluid sample.

In a particular embodiment, step c) is carried out by subtracting the spectral component associated with metHb, which is obtained by normalization of a standard differential spectrum $SDR^{KCN}$ with the measured differential spectrum $SD^{KCN}$, wherein said normalization is carried out with respect to said absorption spectrum by calculating a normalization coefficient K2 at a wavelength between about 350 nm and about 700 nm, preferably between about 380 nm and about 440 nm.

Advantageously, the normalization coefficient K2 is calculated by determining the ratio between the values of $SD^{KCN}$ and $SDR^{KCN}$ preferably by measuring for each differential spectrum the difference between (i) $DO_{max}$ and $DO_{min}$, and $DO^R_{max}$ and $DO^R_{min}$, (ii) $DO_{max}$ and $DO^R_{max}$, or (iii) $DO_{min}$ and $DO^R_{min}$.

Generally, the normalization coefficient K2 takes into account the dilution factor of the biological fluid.

Alternatively, the normalization coefficient KDS2 may be calculated on the same principle except that instead of taking into account the spectral difference of a spectrum before and after adding KCN, it is the second derivative of the spectral difference that is used for the biological sample and for the metHb sample.

Apart from KCN, NaCN or $NaN_3$ may also be used to assay metHb, according to the same principle as described above for KCN.

At this step, only metHb is assayed because of its strong affinity for the $CN^-$ or $N_3^-$ anion. The concentration of KCN and NaCN stock solutions used may be, for example, 50 mM and that of $NaN_3$, for example 100 mM. Advantageously, the final concentration of KCN is between 100 and 500 μM, preferably between 150 μM and 250 μM, more preferably about 200 μM. Advantageously, the final NaCN concentration may lie between 100 to 500 μM, preferably between 150

µM and 250 µM, more preferably about 200 µM. Advantageously, the final concentration of $NaN_3$ lies between 0.5 to 1 mM.

The incubation time for metHb and cyanide is about 5 minutes before assaying in plasma.

Step d)

Step d) consists in the subtraction from said intermediate calculated spectrum SC2 of a spectral component associated with bilirubin in order to obtain an intermediate calculated spectrum SC3.

In a particular embodiment, step d) is carried out by the subtraction from the spectral component associated with bilirubin, obtained by normalization of a reference spectrum SR3 of bilirubin linked to the serum albumin, said normalization being carried out with respect to said intermediate calculated spectrum SC2 by calculating a normalization coefficient K3 at a wavelength comprised in all or part of the ultraviolet, and all or part of the visible, preferably a wavelength ranging from about 350 nm to about 700 nm.

Advantageously, the normalization coefficient K3 is calculated by determining the ratio between the values of the second derivatives of the calculated spectrum SC2 and the standard spectrum SR3 at a wavelength comprised in all or part of the ultra-violet, and in all or part of the visible, preferably at a wavelength ranging from about 350 nm to about 700 nm, more preferably at a wavelength ranging from about 440 nm to about 540 nm, even more preferably about 501 nm.

Thus, SC3 may be calculated as follows:

$$SC3 = SC2 - K3 \times SR3 \text{ at } \lambda \epsilon [440 \text{ nm}, 540 \text{ nm}]$$

where:

SR3 is the reference spectrum for bilirubin, and $\lambda \epsilon [440 \text{ nm}, 540 \text{ nm}]$ means that the wavelength lies between 440 nm and 540 nm.

In addition:

$$K3 = \left(\frac{d^2 SC2}{d\lambda^2}\right) \bigg/ \left(\frac{d^2 SR3}{d\lambda^2}\right)$$

In another particular embodiment, step d) is carried out by subtracting the spectral component associated with bilirubin, and that is obtained by normalization of a reference spectrum SR3 of bilirubin linked to serum albumin, said normalization being carried out with respect to said intermediate calculated spectrum SC1 by calculating a normalization coefficient K3 at a wavelength comprised in all or part of the ultraviolet, and all or part of the visible, preferably a wavelength ranging from about 350 nm to about 700 nm.

K3 may therefore be calculated as follows:

$$K3 = \left(\frac{d^2 SC1}{d\lambda^2}\right) \bigg/ \left(\frac{d^2 SR3}{d\lambda^2}\right)$$

By "standard SR3 spectrum of bilirubin" or "standard spectrum SR3" is meant an absorption spectrum of a sample of bilirubin with an excess of serum albumin, i.e. a sample comprising only, or almost only, bilirubin and an excess of serum albumin. The excess of serum albumin allows us to obtain bilirubin linked to serum albumin or "bilirubin/serum albumin". Samples comprising only, or almost only, human bilirubin are commercially available, for example from Sigma Aldrich. For example, bilirubin may be dissolved in 0.1 N NaOH soda and protected from light before being added to a 0.2 µM filtered serum albumin solution for a final 1:2 mole to mole mixture. After 20 minutes of equilibration protected from light, the spectrum of bilirubin/serum albumin is recorded. Advantageously, the sample, comprising only, or almost only, bilirubin/serum albumin, is buffered at a pH of less than 8, preferably between 7.35 and 7.45, more preferably equal to 7.4, and preferably at a pH that is identical to the pH of the biological fluid sample.

Step e)

Step e) consists in the subtraction from said intermediate calculated spectrum SC3 of a spectral component associated with the haem linked to serum albumin (haem/serum albumin) in order to obtain an intermediate calculated spectrum SC4.

In a particular embodiment, step e) is carried out by subtracting the spectral component associated with the haem/serum albumin, obtained by normalization of a reference spectrum SR4 of haem/serum albumin, said normalization being carried out with respect to said intermediate calculated spectrum SC3 by calculating a normalization coefficient K4 at a wavelength comprised in all or part of the ultraviolet, and all or part of the visible, preferably in a range of wavelengths ranging from about 200 nm to about 800 nm, more preferably ranging from about 300 nm to about 700 nm, even more preferably ranging from about 380 nm to about 460 nm or between 600 and 700 nm for a high concentration of the species, or in the absence of dilution (≤½) in a pure serum or a plasma taken on citrate to overcome the pH value close to 7.4.

Advantageously, the normalization coefficient K4 may be calculated by determining the ratio between the values of the second derivatives of the absorption spectrum and the reference spectrum SR4 at a wavelength comprised in all or part of the ultra-violet, and all or part of the visible, preferably a wavelength ranging from about 350 nm to about 460 nm.

Thus, SC4 may be calculated as follows:

$$SC4 = SC3 - K4 \times SR4 \text{ at } \lambda \epsilon [350 \text{ nm}, 700 \text{ nm}]$$

where:

SR4 is a reference spectrum of the haem/serum albumin, and $\lambda \epsilon [350 \text{ nm}, 700 \text{ nm}]$ refers to a wavelength between 350 nm and 700 nm.

In addition:

$$K4 = \left(\frac{d^2 SC3}{d\lambda^2}\right) \bigg/ \left(\frac{d^2 SR4}{d\lambda^2}\right)$$

Wherein $\frac{d^2 SC3}{d\lambda^2}$ is the second derivative of the intermediate calculated spectrum SC3 and $\frac{d^2 SR4}{d\lambda^2}$ is the second derivative of the reference spectrum SR4

By "reference spectrum SR4 of haem/serum albumin" or "reference spectrum SR4", is meant an absorption spectrum of a sample of haem/serum albumin, i.e. a sample comprising only, or almost only, haem/serum albumin as a protein. Haem and serum albumin samples are available, for example, from Sigma Aldrich. For example, haem may be dissolved in a 0.1 N NaOH soda solution and protected from light before being added to a solution of serum albumin filtered through 0.2 μM for a final mixture 1:2 mole to mole. After 20 minutes of equilibration protected from light, the spectrum of haem/serum albumin is recorded. Advantageously, the sample, comprising only, or almost only, haem/serum albumin as protein is buffered at a pH of less than 8, preferably between 7.35 and 7.45, more preferably equal to 7.4, and preferably at a pH identical to the pH of the sample of the biological fluid.

In a particular embodiment, step e) is implemented by subtracting the spectral component associated with the haem-serum albumin or with a linear combination of the haem/serum albumin and the haem/haemopexin, obtained by normalization of a reference spectrum SR4 of haem/serum albumin or of the contribution of two reference SR4 of haem/serum albumin and SR5 of haem/haemopexin, said normalization being carried out with respect to said intermediate calculated spectrum SC3 by calculating a normalization coefficient K4 (or K4 and K5) at a wavelength comprised in all or part of the ultraviolet, and all or part of the visible, preferably in a range of wavelengths ranging from about 200 nm to about 800 nm, more preferably ranging from about 300 nm to about 700 nm, even more preferably ranging from about 380 nm to about 450 nm.

In another particular embodiment, the normalization coefficient K4 or K4 and K5 are calculated by determining the ratio between the values of the second derivatives of the intermediate calculated spectrum SC3 and of the reference spectrum SR4 or of the reference spectra SR4 and SR5 (haem/serum albumin and haem/haemopexin respectively) at a wavelength comprised in all or part of the ultraviolet, and all or part of the visible, preferably a wavelength ranging from about 300 nm to about 450 nm.

Step f)

Step f) consists in subtracting from said intermediate calculated spectrum SC4 a spectral component associated with one or more other proteins present in the biological fluid in order to obtain an intermediate calculated spectrum SC5.

Apart from haem/serum albumin, the most desired species for haem binding in the case of weak or even moderate and non-chronic haemolysis or in the case of haem-based therapy (porphyrias), is the haem/haemopexin.

Alternatively, when the protein in step f) is haem/haemopexin, steps e) and f) may be combined as follows:

SC4 may be calculated as follows at I ∈[350, 700 nm], preferably at I ∈[360, 460 nm]:

$$SC4 = SC3 - K4 \times SR4 - K5 \times SR5$$

where: SR4 is the haem/serum albumin reference spectrum, and SR5 is the haem/haemopexin reference spectrum.

K4 and K5 are obtained by simulating (simulation is understood to mean modelling in such a context) the second derivative of SC3 as a linear combination of the two second derivatives of the haem/serum albumin and the haem/haemopexin respectively weighted coefficients K4 and K5:

$$\left(\frac{d^2 SC3}{d\lambda^2}\right) = K4\left(\frac{d^2 SR4}{d\lambda^2}\right) + K5\left(\frac{d^2 SR5}{d\lambda^2}\right)$$

Where:

$$\frac{d^2 SC3}{d\lambda^2}:$$

the second derivative of the intermediate calculated spectrum SC3, $$\frac{d^2 SR4}{d\lambda^2}:$$

the second derivative of the reference spectrum SR4, and $$\frac{d^2 SR5}{d\lambda^2}:$$

the second derivative of the reference spectrum SR5.

The simulation may be performed using the non-linear least squares regression technique or any other type of non-linear simulation algorithm.

By "reference spectrum SR5 of haem/haemopexin" or "reference spectrum SIRS" or "SIRS", is meant an absorption spectrum of a sample of haem/haemopexin, i.e. a sample comprising only, or almost only, haem/haemopexin as protein. Haemopexin samples are available, for example, from Sigma Aldrich. Advantageously, the sample, comprising only, or almost only, haem/haemopexin as protein is buffered at a pH of less than 8, preferably between 7.35 and 7.45, more preferably equal to 7.4, and preferably with a pH identical to the pH of the sample of the biological fluid.

In a particular embodiment, the other protein(s) present in the biological fluid are one or more haem proteins, for example one or more proteins chosen from among $HbO_2$, MetHb, bilirubin, haem/serum albumin, haem/haemopexin, carboxylated haemoglobin (HbCO), a biomarker of haem catabolism by haem oxygenase, myoglobin, porphyrins, bilirubin degradation products, such as degradation products of bilirubin by haem/serum albumin in the presence of reactive oxygen species ($H_2O_2$) (mono-pyrrole isomers (haem-BOXes), di-pyrroles (PDPs) and biliverdin), in the urine porphobilin, stercobilin and urobilin.

It may also be a biological molecule, for example a pharmaceutical molecule administered to a patient.

In a particular embodiment, step f) may be carried out by subtracting the spectral component associated with the other protein(s), obtained by normalization of one or more reference spectra SRX (for example SR5) from the other protein(s), wherein said normalization is carried out with respect to said intermediate calculated spectrum (for example SC5) by calculating a coefficient of normalization KX (for example K5) at a wavelength that those skilled in the art can determine for the other protein(s).

Thus, SC5 may be calculated as follows at I ∈[200,700 nm], for example at 420 nm for HbCO:

$$SC5 = SC4 - K5 \times S5$$

Where:

SR5 is the reference spectrum of another protein or biological molecule, and

I ϵ[200,700 nm] means that the wavelength is between 200 nm and 700 nm.
In addition;
Where:

$$K5 = \left(\frac{d^2SC4}{d\lambda^2}\right) / \left(\frac{d^2SR5}{d\lambda^2}\right)$$

$d^2SC4/dl^2$ is the second derivative of the intermediate calculated spectrum SC4, and
$d^2SR5/dl^2$ is the second derivative of the reference spectrum SR5

In a particular embodiment, the reference spectra of steps b), c), d), e) and f) are obtained from a sample of the different pure species, at a lower maximum optical density (DO) or equal to 2, preferably less than or equal to 1. That is to say, a DO of the reference spectrum of the species whose maximum value is less than or equal to 2, preferably less than or equal to 1. Preferably, the absorption spectra measured are analyzed using the reference spectra in purple for the MetHb, haem/serum albumin and haem/haemopexin species in blue-green for unconjugated and conjugated bilirubin, and in yellow for $HbO_2$ but also in the red for haem/serum albumin.

It is well known to those skilled in the art that there is a proportionality relationship between the absorbance and the concentration of the species that we wish to determine.

This proportionality relationship meets the following equation:

$$A = \xi l \, c$$

Where:
ξ is the extinction coefficient which depends on the wavelength;
I is the length of the tank (generally 1 cm), and
c is the concentration of the reference solution.

In a particular embodiment, the optical density DO is equal to the absorbance A, i.e.:

$$A = DO$$

In a preferred embodiment the optical density DO is equal to 1, which corresponds to $$A = DO = 1$$

There is therefore a proportionality between the absorbance or the optical density DO and the concentration, where A=DO.

By "extinction coefficient" is meant the absorbance value of a species in a solvent and/or a solute at a given temperature normalized at a concentration and an optical path. The extinction coefficient is also called the molar extinction coefficient, the unit of which is generally given in $mM^{-1}$ $cm^{-1}$.

The extinction coefficients are normalized values known to those skilled in the art. For example, the extinction coefficients associated with the reference species that make it possible to calculate the concentrations of each of the species in the biological fluid, are:
at 577 nm: extinction coefficient of 15.5 $mM^{-1}$ $cm^{-1}$ for $HbO_2$;
at 403-404 nm: extinction coefficient of 92 $mM^{-1}$ $cm^{-1}$ for haem/serum albumin of human origin;
at 404-424 nm: extinction coefficient of 160 $mM^{-1}$ $cm^{-1}$ for the spectral difference of the MetHb±CN;
at 540 nm: extinction coefficient of 11.5 $mM^{-1}$ $cm^{-1}$ for metHb-CN⁻;
at 459 nm±1 nm: extinction coefficient of 47 $mM^{-1}$ $cm^{-1}$ for unconjugated bilirubin;
at 413-414 nm: extinction coefficient of 120 $mM^{-1}$ $cm^{-1}$ for haem/haemopexin, and
at 420 nm: extinction coefficient of 190 $mM^{-1}$ $cm^{-1}$ for HbCO.

These extinction coefficients make it possible to calculate the concentration of the species for said reference spectrum. For example, the extinction coefficient relative to $HbO_2$ makes it possible to calculate the concentration of pure $HbO_2$ relative to the spectrum SR1.

Thus, the concentrations of the reference solutions X are calculated as follows:

$$c[\text{reference solute } x] = \frac{A}{\xi l}$$

The DO values (close to 1), ϵ and I (1 cm) are known.
We therefore deduce C [reference solute x].

In a preferred embodiment, we obtain an optical density DO for a concentration of a species X, chosen from among $HbO_2$, metHb, bilirubin, haem/serum albumin, haem/haemopexin. For the other species mentioned, some are well referenced in the literature, such as myoglobin or certain haemoproteins, while others must be calculated after dilution in the biological fluid, their concentration being estimated by weighing or, finally, from biological samples in which they are well characterized or predominant.

Without limitation, the concentration thus obtained may be normalized to 10 μM, 100 μM or 1 mM ($mM^{-1}$ $cm^{-1}$). This normalization is a normalization corresponding to an easy-to-use concentration, which makes it possible to normalize the reference spectrum to a given easy-to-use concentration.

Once this known concentration [c ref sol] is normalized, the second derivative of the species of interest of the sample of biological fluid is calculated by determining an amplitude relationship between the measured second derivative and that of the reference:

For example:

$$[HbO2] = \left(\frac{d^2SA}{d\lambda^2}\right)_{577\,nm} \cdot f_{PBS} \cdot f_{dilution} / \left(\frac{d^2SR1}{d\lambda^2}\right)_{577\,nm} \cdot [c \text{ ref sol of } HbO_2]$$

Where:
f PBS is the plasma dilution factor in PBS (phosphate-buffered saline): f PBS=(sample volume+PBS volume)/(sample volume), and
f dilution is the dilution factor of the biological fluid in a possible solute.

The amplitude ratio between the second derivative and that of the reference is at the same wavelength, for example about 577 nm for $HbO_2$.

In particular, when the biological fluid is plasma, unlike serum, the factor of dilution of the blood in the anticoagulant is taken into account. For example, the volume of anticoagulant in a citrated collection tube is 300 μl of solution for a collection volume of 3 ml of blood. The dilution factor is calculated as follows:

$$f_{dilution} = \frac{(1 - Htc) \times (\text{volume of the sample})}{(1 - Htc) \times (\text{volume of the sample}) - \text{volume of solute}}.$$

For a haematocrit (Htc) of 0.4, the dilution factor (multiplying factor) of the concentrations of the species measured will be of the order of 1.2. This factor will decrease to 1.1 for patients with haemolytic anaemia. It should be noted that the other commonly used coagulants (heparin or EDTA) do not induce dilution. More generally, any dilution factor due to the presence of solute in a collection tube, but also between the biological source and the tube (for example during a CEC or ECMO in the extra-corporeal system), must be taken into account. In the latter case, an internal marker that is stable over time may be chosen to estimate the dilution as the total protein concentration before circulation. This point is valid for all biological fluids. It is also possible in some cases to take into account the infusion of a solute in a patient and/or to measure volumetrically the expansion of a fluid, for example, for the urine when these data are available.

Preferably, a dilution of the biological fluid is made at least to ½, preferably in a plasma to $\frac{1}{6}^{th}$ in a 1 cm tank (100 µl of biological fluid →500 µl PBS pH 7.4: 50 mM phosphate of potassium 50 mM NaCl); The measurement will be adjusted for atypical samples if the signal is too weak or too intense as a result:

For example, $$[HbO_2] = \left(\frac{d^2SA}{d\lambda^2}\right)_{577\,nm} \cdot f_{PBS} \cdot f_{dilution} \bigg/ \left(\frac{d^2SR1}{d\lambda^2}\right)_{577\,nm} \cdot [c\ ref\ sol\ of\ HbO_2]$$
$$(\times [HbO_2\ ref])$$

×6 (dilution in PBS)×1.17 (dilution in citrate for an Htc of 0.3).

Or a correction factor of 7 compared to the measured values.

Finally, the concentration of free haemoglobin in plasma must be corrected by the fraction irreversibly linked to haptoglobin. Even if the HbO$_2$ is generally the majority (>90%), we should calculate the total Hb=HbO$_2$+MetHb+HbCO. In fact, there is no spectral difference between haemoglobin (i.e. HbO$_2$) in plasma, free or complexed with haptoglobin. In addition, only the free fraction is harmful to the organism. The measurement of haptoglobin if it is expected (most often depleted in patients with chronic haemolysis) is carried out by biochemical reaction with an antibody. It is given in g/l and the average molecular weight of the various isoforms binding 2 dimers of haemoglobin is about 85 kD (i.e. content of the molecular weight of the haemoglobin 64.5 kD: 1.3 g of haptoglobin binds 1 g of tetrameric haemoglobin).

Use

The invention also relates to the use of the spectral data obtained by the method of the invention for determining the content of one or more proteins present in the biological fluid chosen from among HbO$_2$, MetHb, conjugated and non-conjugated bilirubin, haem/serum albumin, haem/haemopexin, carboxylated haemoglobin (HbCO), a biomarker of haem catabolism by haem oxygenase, a haem degradation/oxidation product, a protein/haem complex and a biological molecule.

The determination of the content of one or more proteins present in a biological fluid may be implemented by a processor of a computer system. This computer system may include computer storage means in which instructions are stored which, when executed by the computer system processor, will perform the optical density (comparison.

Generally, those skilled in the art know how to adjust the parameters of the spectrometer, so as to directly obtain the content of one or more proteins present in the biological fluid.

The spectral study method thus provides access to a plurality of protein contents.

Applications

Many applications of this method of determination may be envisaged.

In particular, applications related to haem-related diseases may be developed, i.e.

the disease involving a haem disorder at least as a symptom. Haem-related diseases include haemoglobin-related diseases or red blood call diseases.

Where appropriate, the applications are in vitro applications.

Prediction Method

For this application, a method is proposed that makes it possible to predict that a subject is at risk of suffering from a disease related to the haem or to a haemoprotein.

The prediction method comprises a step for implementing the steps of the method for determining at least one protein content in a biological sample of the subject, so as to obtain determined parameters.

The prediction method also includes a step of predicting that the subject is at risk of suffering from haem or haemoprotein-related disease based on the determined parameters.

Diagnosis Method

This application corresponds to a method for diagnosing a disease linked to a haem or a haemoprotein.

The diagnostic method comprises the implementation of the steps of the method for determining at least one protein content in a biological sample of the subject, so as to obtain determined protein contents.

The diagnostic method also comprises carrying out a step of diagnosing a disease related to the haem or to a haemoprotein on the basis of the determined protein content.

Treatment Method

This application corresponds to a method of treatment of a disease related to the haem or to a haemoprotein (monitoring).

The treatment method comprises the implementation of the steps of the method for determining at least one protein content in a biological sample of the subject, so as to obtain determined protein contents.

The treatment method also comprises the administration of a drug (bone marrow transplant, gene therapy) treating disease related to the haem or to a haemoprotein based on the determined protein content.

Stage Definition Method

In this application, a method is proposed for defining the stages of a disease related to the haem or to a haemoprotein.

The stages of a disease are the different levels of a disease. The definition of the stages is generally defined according to the symptoms of the disease. The definition method comprises the implementation of the steps of a method for determining at least one protein content in a biological sample of the subject, so as to obtain determined protein contents.

The definition method then comprises the definition of the stages of the disease linked to the haem or to a haemoprotein on the basis of the determined protein contents.

Method for Identifying a Target

This application corresponds to a method for identifying a therapeutic target for the prevention and/or treatment of a disease related to the haem or to a haemoprotein.

The identification method comprises the implementation of the steps of the method for determining at least one protein content in a biological sample of images of a first subject, the first subject being a subject suffering from the disease linked to the haem or a haemoprotein.

The identification method also comprises the implementation of the steps of the method for determining at least one protein content in a biological sample of a second subject, in order to obtain a second determined protein content, the second subject being a subject not suffering from a haem or haemoprotein related disease.

The identification method further comprises a step of selecting a therapeutic target based on the comparison of the first determined protein content and the second determined protein content.

Method for Identifying a Biomarker

In this application, a method of identifying a biomarker is proposed.

The biomarker may be a biomarker among the following: a diagnostic biomarker of a disease related to the haem or to a haemoprotein, a susceptibility biomarker of a disease related to the haem or to a haemoprotein, a prognostic biomarker of a related disease related to the haem or a haemoprotein, or a predictive biomarker in response to treatment of a disease related to the haem or to a haemoprotein.

The identification method comprises the implementation of the steps of the method for determining at least one protein content in a biological sample from a first subject, in order to obtain a first determined content, wherein the first subject is a subject suffering from the haem or haemoprotein related disease.

The identification method comprises the implementation of the steps of the method for determining at least a first determined protein content in a biological sample of images of a second subject, in order to obtain a second determined protein content, wherein the second subject is a subject not suffering from a disease related to the haem or to a haemoprotein.

The identification method comprises selecting a biomarker based on the comparison of the first determined protein content and the second determined protein content.

Method for Screening a Compound

This application corresponds to a method for screening a compound.

The compound is a drug.

The drug has an effect on a known therapeutic target, so as to prevent and/or treat a disease related to the haem or to a haemoprotein.

The screening method comprises the implementation of the steps of the method for determining at least one protein content in a biological sample of a first subject, in order to obtain a first determined protein content, wherein the first subject is a subject suffering from the haem or haemoprotein related disease and having received the compound. In this context, the term "receive" comprises all modes of drug administration.

The screening method also comprises the implementation of the steps of the method for determining at least one protein content in a biological sample from a second subject, in order to obtain a second determined protein content, wherein the second subject is a subject suffering from the haem or haemoprotein related disease, but who did not receive the compound.

The screening method further comprises selecting a compound based on the comparison of the first determined protein content and the second determined protein content.

Qualification or Disqualification Method

This application corresponds to a method for qualifying and disqualifying blood bags.

The bags are containers.

The bags contain a biological sample of the subject.

The qualification or disqualification method comprises the implementation of the steps of the method for determining at least one protein content in the medical bag, in order to obtain determined protein contents.

The qualification or disqualification method also includes the qualification or disqualification of medical bags based on the determined protein contents. For example, if the protein content shows that the quality of the sample is so degraded that the sample can no longer be used, the bag is disqualified. The idea of such a specific application is to analyze the content of haemolysis in the conservation medium, but also if there exists any doubt about collecting red blood cells for incubation in an isotonic PBS at pH 7.4 (the pH of the bags decreases) with the storage time and is generally between 6 and 7) in the presence of albumin 100-500 µM (in vivo) to recover all that could interact with the membrane, and also to measure the most fragile component that might reduce the transfusion yield. Hence this application is part of the quality control.

Method of Monitoring a Treatment

This application corresponds to a method for monitoring a treatment against the disease linked to the haem or to a haemoprotein in a subject suffering from the disease linked to haemoglobin and having received the treatment.

The monitoring method comprises the implementation of the steps of the method for determining at least one protein content in a biological sample of the subject, in order to obtain determined protein contents.

The monitoring method further comprises monitoring the determined protein contents with the monitoring of a treatment against a haem or haemoprotein related disease in a subject suffering from the haem or haemoprotein related illness, and who received the treatment.

Such applications correspond to many possible applications, some of which will be described below.

The method may, in particular, be used in:
monitoring the treatment of porgin haem arginate;
monitoring treatment with purified or recombinant haemopexin;
monitoring the addition of an haemoglobin-derived blood substitute;
monitoring of treatments inducing haemolysis such as ECMO (extra-corporal membrane oxygenation, haemodialysis or cardiac prostheses);
characterization of plasma exchanges, of plasmapheresis (clearance of haemoglobin and haem after addition of their natural sensors, haptoglobin and haemopexin), calculation of the exchange yield (dilution of the patient's plasma), and
use of the concentration of the haem not linked to haemopexin which may be involved in redox reactions linked to HSA (human serum albumin), or which may diffuse towards the tissues and modify tissue homeostasis.

In conclusion, a method has been proposed for determining at least one protein in the blood which is more precise, while remaining simple to implement. This allows us to take into account many applications for diseases related to haem and haemoglobin.

Conclusions:

The spectral characteristics of the different species to be assayed are therefore unique. By using a biochemical reaction of a species in order to induce a specific spectral change for its assay and/or by using a most appropriate sequential mathematical approach to assay each species from a spectrum of plasma or serum, it is therefore possible to measure in vitro the status of biomarkers of haemolysis in vivo, more particularly of the intravascular component and/or dyserythropoiesis. More generally, these biomarkers may be linked to a pathology associated with a defect in the anabolism and/or catabolism of the haem and the haemoglobin.

EXAMPLES

Example 1 (FIG. 1)

UV/visible absorption spectrum of a DHTR patient. The different species linked to the haem were measured by a mathematical approach based on experimental spectral measurements coupled to the spectra of the pure forms of each species considered.

Figure 5A:
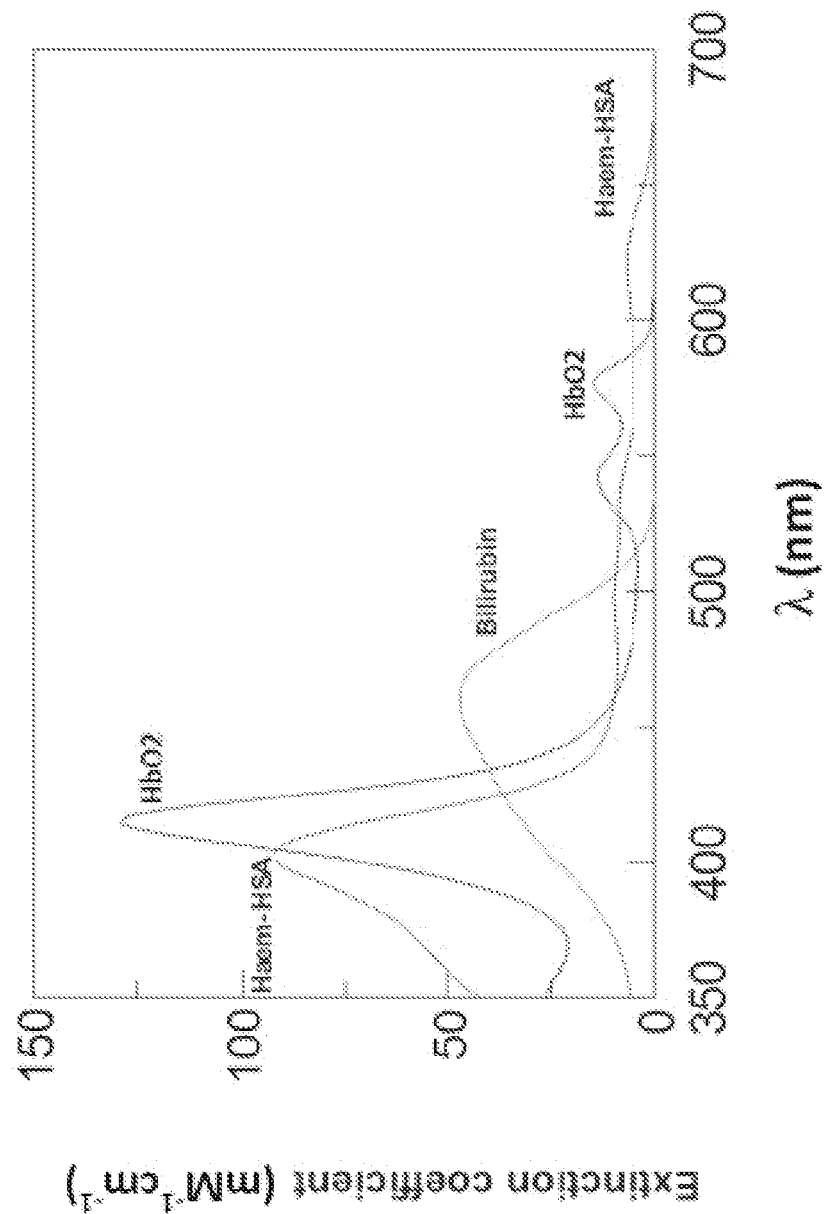
FIGS. 5a, 5h, 5c, 5d and 5e: Standard spectra of $HbO_2$, haem-HSA, bilirubin, metHb±KCN, haem-Hx and their associated second derivatives.
Figure 5B:
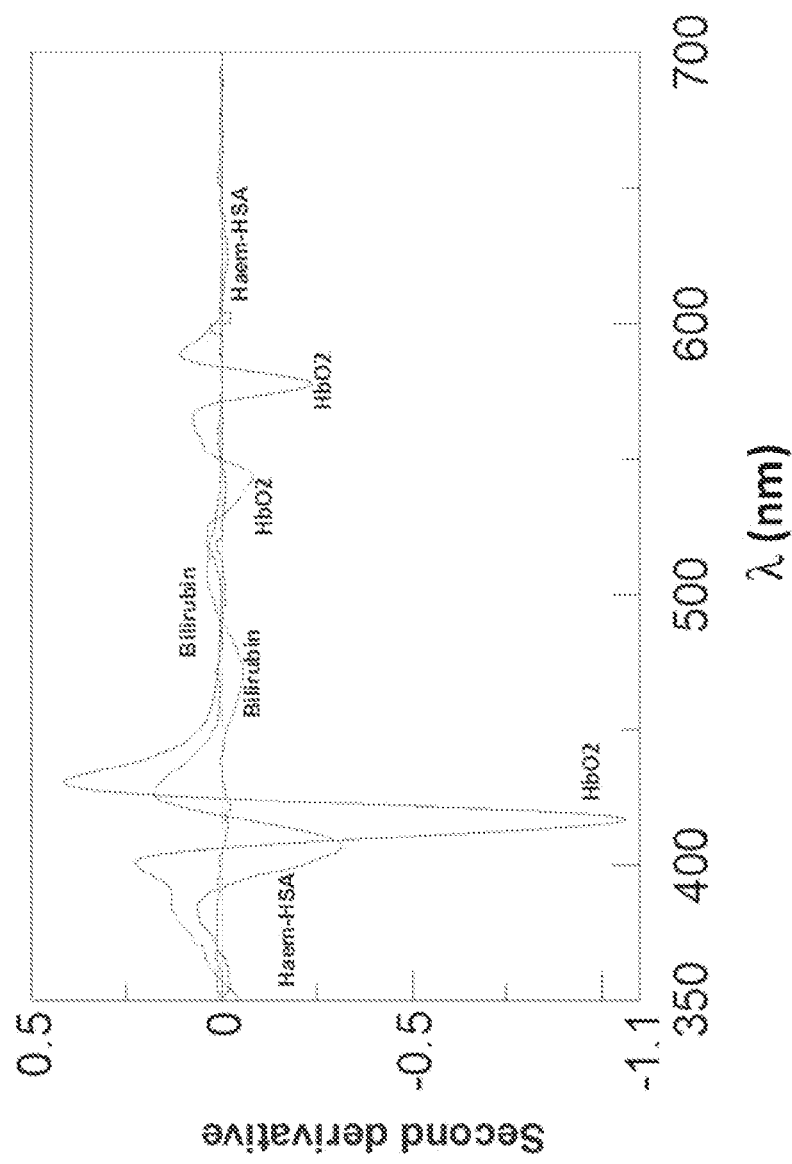

Materials and methods: plasma diluted $\frac{1}{6}^{th}$ (optical path 4 mm) in a PBS 50 mM potassium phosphate 50 mM NaCl pH 7.4. Addition of 0.2 mM KCN from a 50 mM stock solution. Or 2.5 µl in 600 µl total of diluted plasma (dilution factor 1.004).

first absorption spectrum: measured spectrum of plasma second intermediate calculated spectrum: the $HbO_2$ component was removed by subtraction of a completely oxygenated haemolysate spectrum in air (see FIG. 5a) based on the second derivative between 500 and 600 nm (typically, the peak at 577 nm presents an intense negative band for the second derivative). In fact, the narrow peaks in this absorption domain only come from the $HbO_2$ spectrum while the other major spectral components present here (bilirubin, metHb ($HbFe^{3+}$) and haem-HSA) have less intense second derivatives because of their large peaks. HSA=human serum albumin.

third calculated intermediate spectrum: the bilirubin component was removed after subtracting the spectrum of bilirubin linked to HSA (see FIG. 5a) based on the second derivative between 440 nm and 520 nm (FIG. 5b).

fourth calculated intermediate spectrum: after recording a second spectrum of the same plasma after adding KCN to induce a change in the specific absorption of this species after binding to CN of ferric iron, the methaemoglobin (metHb) component was subtracted once its assay was performed (see FIGS. 4, 5a, 5b, 5c and 5d). It should be noted that in the event of a strong contribution from the metHb component, its subtraction is made before that of bilirubin or even before that of $HbO_2$. At this stage, the residual spectrum is mainly due to what is called free haem which is, in fact, metalbumin or haem-HSA for plasmas of patients with chronic haemolysis or strong haemolysis.

However, haem-haemopexin (haem-Hx) may be present but always in a lower quantity due to the concentration ratio between HSA and haemopexin ≥40 under normal conditions which is increased due to haemolysis by rapid clearance of the haem-haemopexin complex by hepatic endocytosis until its depletion of the plasma as in the examples presented. The calculation of the haem-HSA concentration was made from the second derivative of the spectrum taken between 390 nm and 440 nm (typically the peak at 403-404 nm gives a negative band of the second derivative shifted to 406 nm, see FIG. 5e). It should be noted that the second derivative of haem-haemopexin is more intense than haem-HSA (FIG. 5e). The presence of 10-20% of haem-haemopexin results in a significant displacement of the minimum of the second derivative measured, towards that of the haem-haemopexin. In this case, the second derivative measured may be simulated as a linear combination of the two major protein complexes in vivo for the binding of the plasma haem.

Fifth calculated intermediate spectrum: the residual absorption spectrum calculated after subtracting the spectral contribution of haem-HSA (depletion of haemopexin). This spectroscopic analysis is not restricted to the haem-related species listed above; for example, myoglobin in the case of myolysis may be measured.

Results: The values of haemolysis are listed in the figure: for $HbO_2$, MetHb, total bilirubin, the plasma haem mainly bound to HSA. Since the sample is taken at a distance from the peak of haemolysis (+24h) the dosage of haem is probably a reflection of the status of haemolysis just after the transfusion and before the massive haemolysis which is usually followed by very high haemoglobinuria. In fact, the absence of binding of the haem to haemopexin indicates de facto its quasi-depletion of the vascular compartment. The clearance of the haem is thus greatly slowed down.

Conclusions: The measurement of plasma haem raises the question of the role of haemolysis in sickle cell anaemia increased by haemolysis after transfusion of red blood cell concentrates, a population of which is weakened after storage, on major post-transfusion haemolysis. In fact in some DHTRs, there is the absence of detectable antibodies against the donor red blood cells. Haemolysis before DHTR could, for example, induce activation of the alternate complement pathway.

[Free plasma $Hb$]=[Total $Hb$, in haem]−[Haptoglobin,$g/l$]/85000×4

The extinction coefficient at 577 nm for the $HbO_2$ absorption spectrum is 15.5/mM/cm.

The ratio (metHb ($GbFe^{3+}$)+haem ($Fe^{3+}$) in plasma)/total haem may be used as an index of oxidative stress in plasma.

Example 2 (FIGS. 2a, b, c, d): Assay on a Sample of Sickle Cell Patient with a Mechanical Heart Valve Problem After subtraction of the different spectral components using the second derivatives for $HbFe^{2+}(O_2)$, bilirubin-HSA and the determination of $HbFe^{3+}$ after addition of KCN, the presence of plasma haem was revealed in purple here in a sickle cell patient with a mechanical heart valve problem (FIG. 2a).

Materials and methods: plasma diluted $\frac{1}{6}^{th}$ (optical path 4 mm) in a PBS 50 mM potassium phosphate 50 mM NaCl pH 7.4. Addition of 0.2 mM KCN from a 50 mM stock solution. Or 2.5 µl in 600 µl total of diluted plasma (dilution factor 1.004).

Results: following the same methodology as in FIG. 1, the biomarker values for haemolysis are: plasma haemoglobin 13 µM (5% $Fe^{3+}$), total bilirubin 130 µM, plasma haem 15 µM. Likewise, the absence of binding of the haem to haemopexin indicates a virtual depletion of this "scavenger" of the haem.

In the insert is shown the second derivative of the spectral form excluding globin (dotted line), and which corresponds well to the presence of plasma haem linked to HSA (solid line).

Conclusions: The haemolysis biomarker assay may be used to diagnose and quantify the impact of this mechanical haemolysis. Other haemolysis of this type may be followed by haemolysis as in the case of CEC (cardiac surgery for example), artificial heart.

Figure 2B:
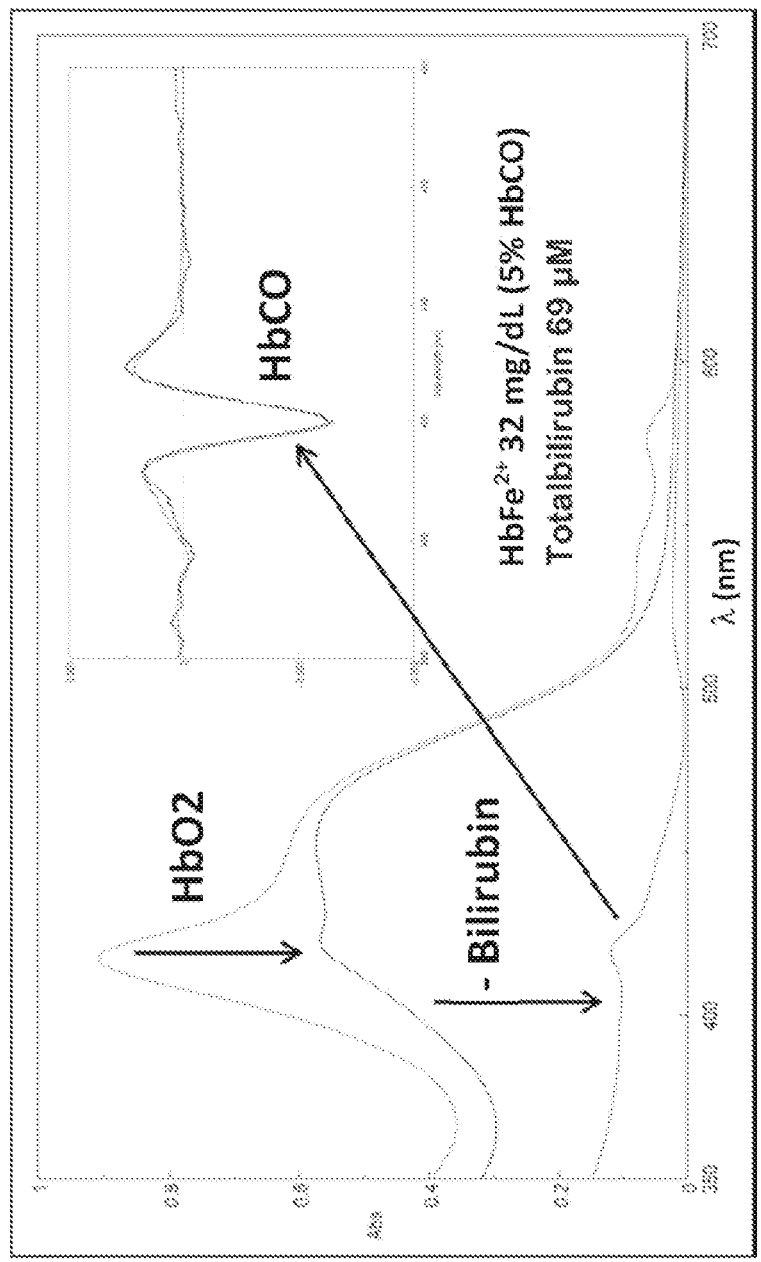
FIG. 2b: Method for assaying haemoglobin $Fe^{2+}O_2$, $Fe^{3+}$CO and $Fe^{3+}$(not 25 detectable), plasma haem and haem degradation and oxidation products by a UV/visible spectrophotometric approach on a plasma sample from a patient with sickle cell disease and moderate haemolysis under hydroxyurea.

Assay on a sample of sickle cell anaemia patient with moderate haemolysis under HU (FIG. 2b)

Materials and methods: plasma diluted $\frac{1}{6}^{th}$ (optical path 1 cm) in a PBS 50 mM potassium phosphate 50 mM NaCl pH 7.4. Addition of 0.2 mM KCN from a 50 mM stock solution. Or 2.5 µl in 600 µl total of diluted plasma (dilution factor 1.004).

Results: following the same methodology as in FIG. 1, the values of the haemolysis biomarkers are given in the figure. After subtraction of the different spectral components using the second derivatives for $HbFe^{2+}(O_2)$, bilirubin-HSA and the $HbFe^{3+}$ assay after addition of KCN (not present; haem plasma <1 µM), the presence of HbCO was revealed in purple here in a sickle cell patient under hydroxyurea with moderate haemolysis but, however, 10 times higher than the average of sickle cell patients with low intravascular haemolysis (FIG. 2b). In the insert is shown the second derivative of the spectral component in purple after subtraction of $HbO_2$ and bilirubin linked to HSA in comparison with the reference of HbCO.

Conclusions: the absence of plasma haem could result from a strong haem-oxygenase activity revealed by the presence of HbCO or from an effect of treatment with hydroxyurea (reduction of sickle-forming and dehydration of red blood cells).

Assay on a sample of sickle cell anaemia patient with moderate haemolysis and an aggravating risk factor.

Materials and methods: plasma diluted $\frac{1}{6}^{th}$ (optical path 1 cm) in a PBS 50 mM potassium phosphate 50 mM NaCl pH 7.4. Addition of 0.2 mM KCN from a 50 mM stock solution. Or 2.5 µl in 600 µl total of diluted plasma (dilution factor 1.004).

Figure 2C:
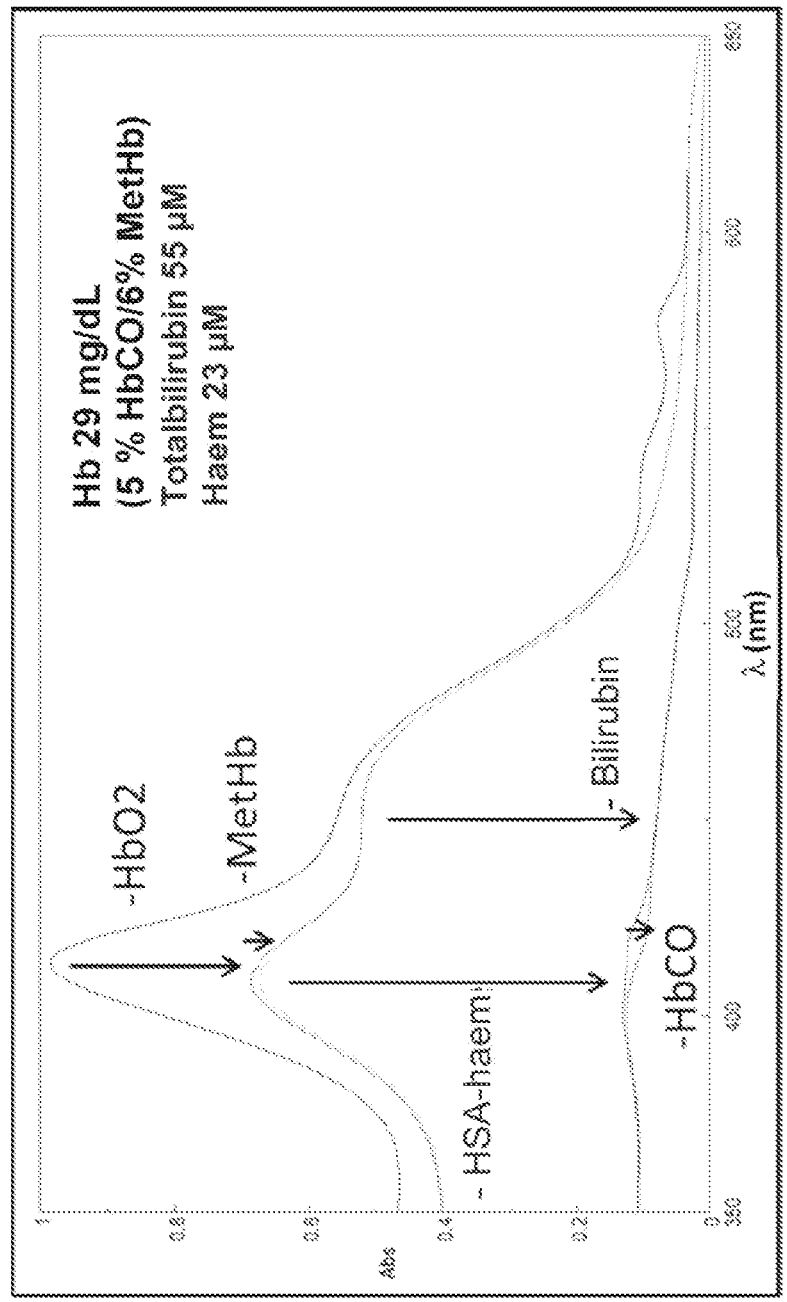
FIGS. 2c and 2d: Method for assaying haemoglobin $Fe^{2+}O_2$ and $Fe^{3+}$CO and Fe3+, plasma haem and haem degradation and oxidation products by a UV/visible spectrophotometric approach on a plasma sample from a patient with sickle cell anaemia and moderate haemolysis associated with aggravating risk factors: high level of dense red blood cells, G6PD deficiency and pharmaceutical multi-treatments.
Figure 2D:
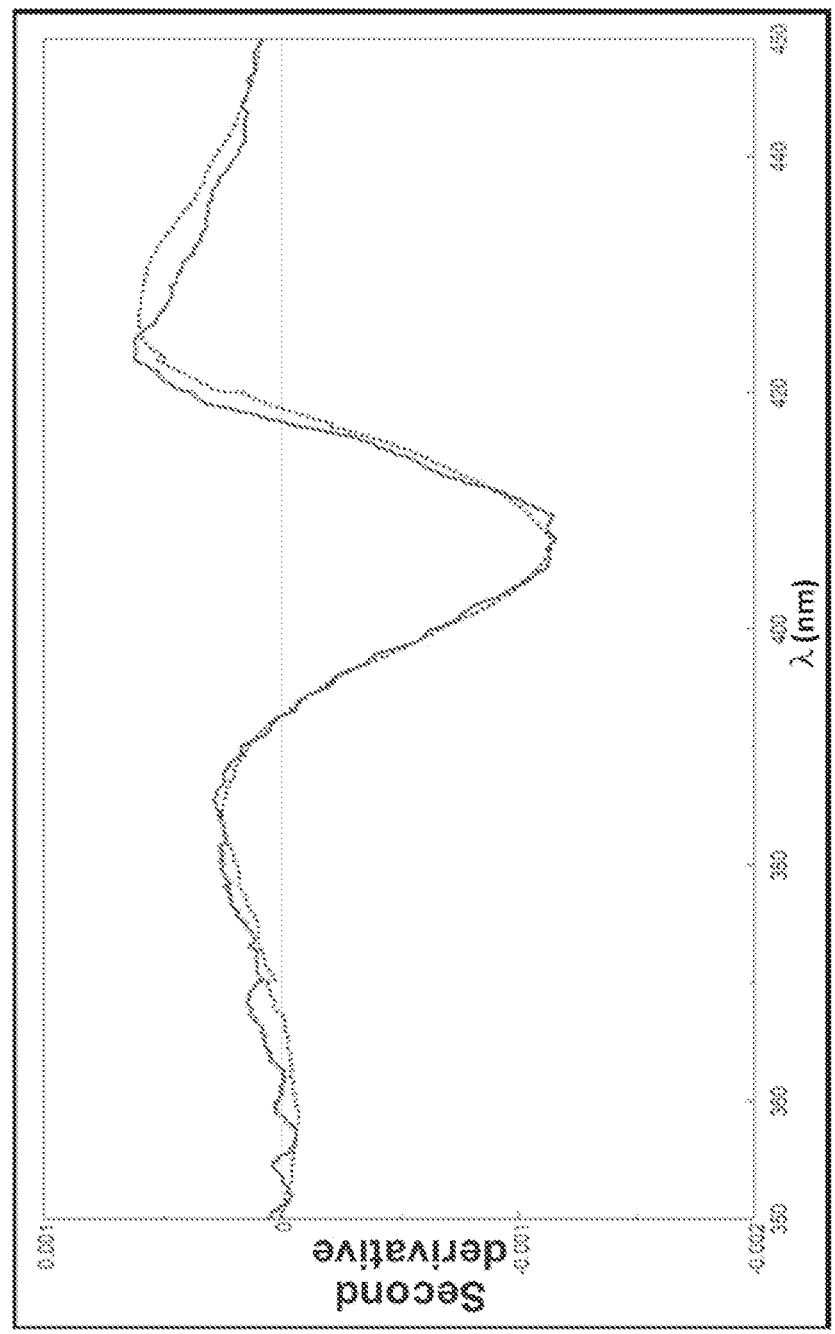

Results: according to the same methodology as FIG. 1, the values of the haemolysis biomarkers are given in FIG. 1. After subtraction of the different spectral components using the second derivatives for $HbFe^{2+}$ ($O_2$) and bilirubin, the $metHbFe^{3+}$ assay after addition of KCN, HbCO (FIG. 2c), the plasma haem linked to HSA (FIGS. 2c and 2d) was revealed in purple here in a sickle cell patient with moderate haemolysis. The presence of plasma haem in this patient with moderate haemolysis is, however, 10 times higher than the average of sickle cell patients without intravascular haemolysis.

Conclusions: In this patient this high amount of plasma haem may be due to several factors which must be considered:
1) the presence of 30% of more haemolytic dense red blood cells and subject to the loss of membrane material via the formation of microparticles,
2) the presence of an enzyme deficiency in G6PD which is responsible for oxidative stress in the red blood cells, and
3) the accumulation of different drug treatments (this analysis of haemolysis may be used as part of longitudinal monitoring of treatment).

Example 3 (FIGS. 3a, b): Determination of Total Plasma Bilirubin

Materials and methods: plasma from a patient with low intravascular haemolysis (hereditary stomatocytosis with dehydration) diluted $\frac{1}{6}^{th}$ (optical path 1 cm) in a 50 mM PBS 50 mM potassium phosphate NaCl pH 7.4. The low spectral contribution of plasma Hb was subtracted as described in FIG. 1. After dissolution of the lyophilized human HSA "fatty free" in this same buffer then addition of bilirubin (<HSA) as described in Example 1 (Sigma products) a reference haem-HSA spectrum is recorded and standardized.

Figure 3A:
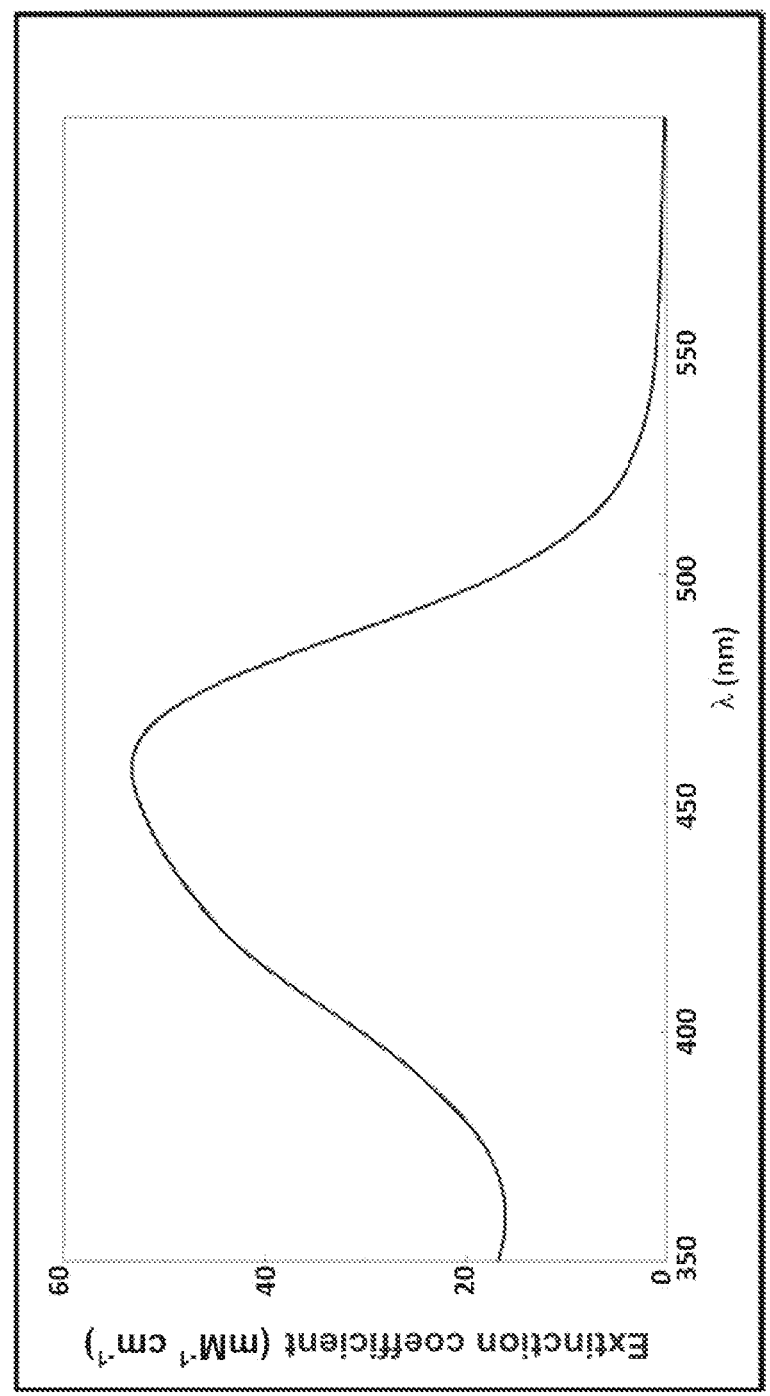
FIGS. 3a and 3b: Method for assaying total plasma bilirubin by UV/visible spectrophotometry.
Figure 3B:
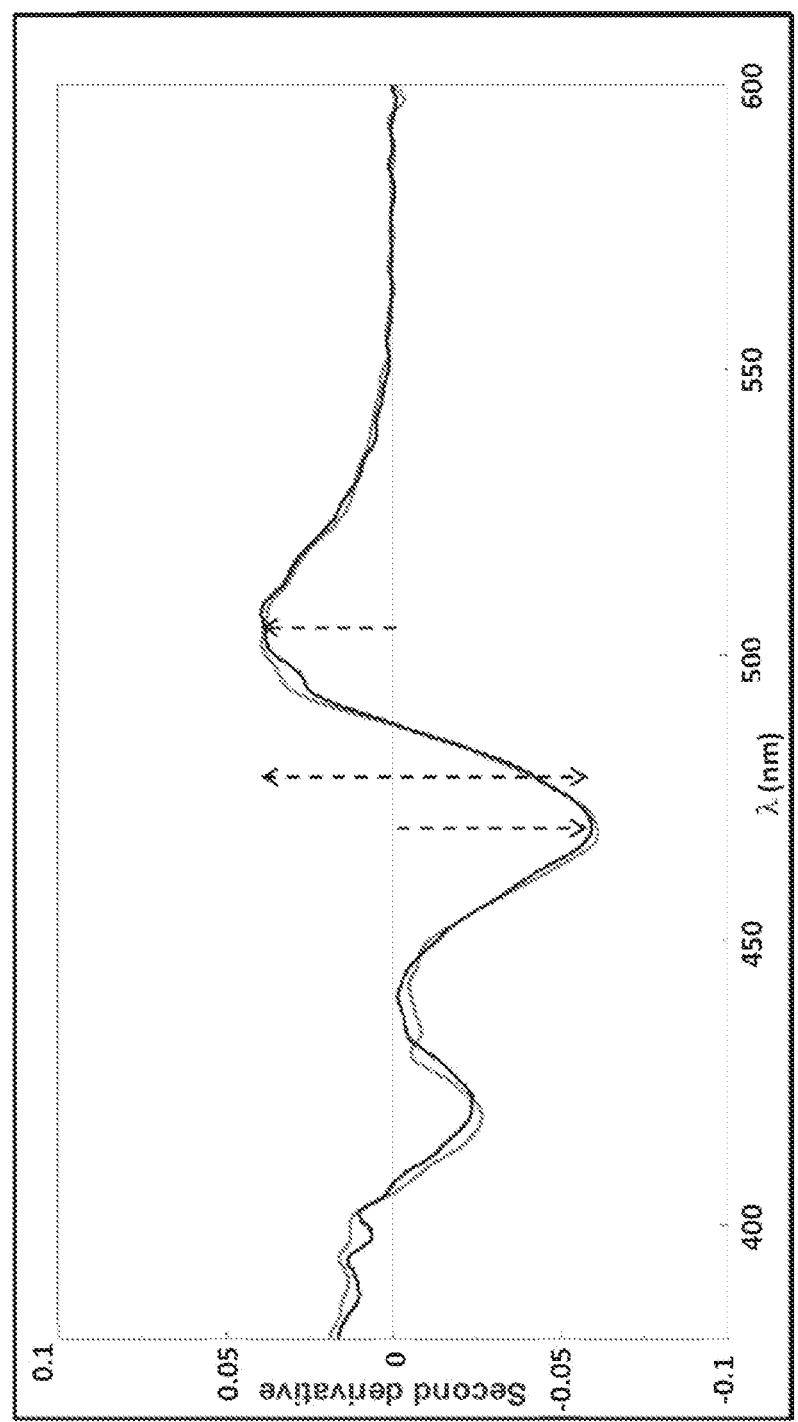

Results: The plasma spectrum after subtraction of $HbO_2$ is shown in FIG. 3a. It corresponds to the spectral form of bilirubin (unconjugated and more weakly conjugated) linked to HSA. This spectrum is similar to that obtained from the reference spectra of bilirubin bound to human HSA (commercial products). In fact the second derivatives are almost identical (FIG. 3b).

Conclusions: The preferable maximum at 501 nm and the minimum at 470 nm or the difference between the two of the second derivative of a plasma, may be analyzed to estimate the concentration of total plasma bilirubin. If all of the spectral contributions related to the haem have been subtracted, the analysis may also be based on a simple measurement of optical density at maximum absorbance using the extinction coefficient of bilirubin-HSA.

Example 4 (FIGS. 5a, b, c, d, e)

Materials and methods: UV/visible absorption spectra of the main spectral species measured in the plasma of a patient with haemolytic anaemia, an intravascular component of which is measured in 50 mM NaCl phosphate buffer, pH 7.4, 25° C.

Results: The normalized standard spectra of $HbO_2$, haem-HSA and bilirubin linked to HSA (molar extinction coefficient $mM^{-1}$ $cm^{-1}$, FIG. 5a) and their associated second derivative (FIG. 5b) show the following features:

$HbO_2$=15/mM/cm at 577 nm (the second derivative showed 2 maxima in purple at 400 nm and 430 nm, and a minimum at 416 nm in green, and also two red minima at 543 nm and 577 nm.

Haem-HSA=92/mM/cm at 403 nm-404 nm (the second derivative showed two maxima at 385 nm and 426 nm and a minimum at 406 nm-407 nm. In the red, a minimum is observed about 625 nm absent of all other majority spectral forms and of which it is possible to take advantage for the measurement of high concentration of haem-HSA in the sample and/or by reducing the plasma dilution to ½).

bilirubin-HSA=47 $mM^{-1}$ $cm^{-1}$ at 459±1 nm (for the second derivative, the minimum has been moved to 470 nm and the maximum to 507 nm).

Figure 4:
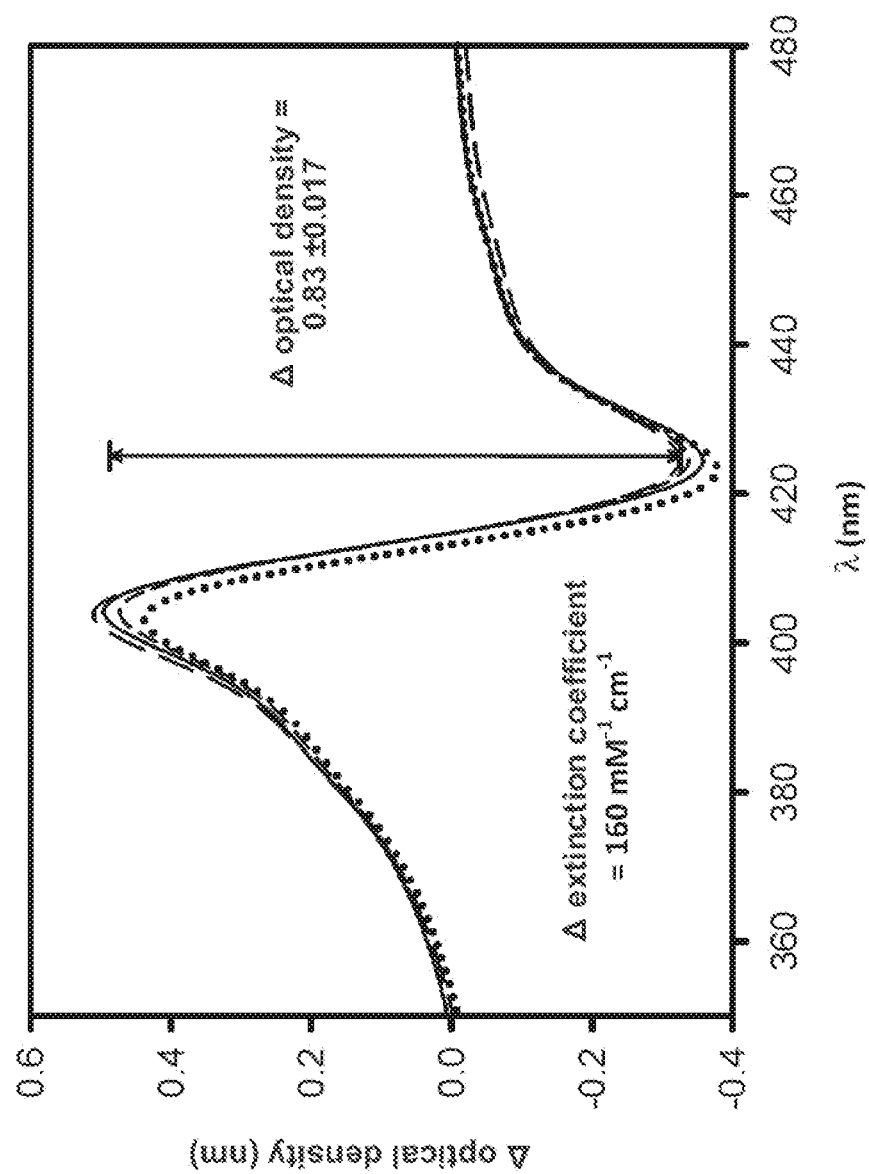
FIG. 4: Determination of haemoglobin $Fe^3$+plasma by UV/visible spectrophotometry using KCN.
Figure 5C:
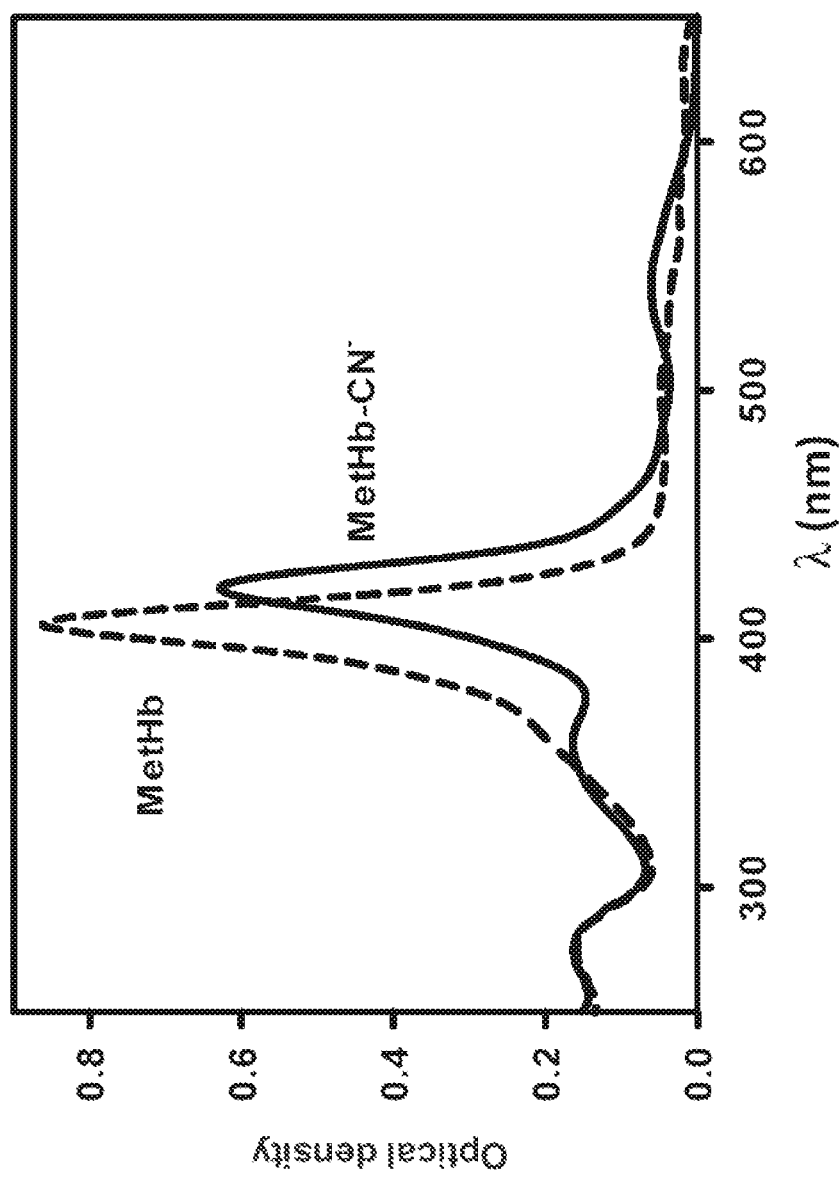
Figure 5D:
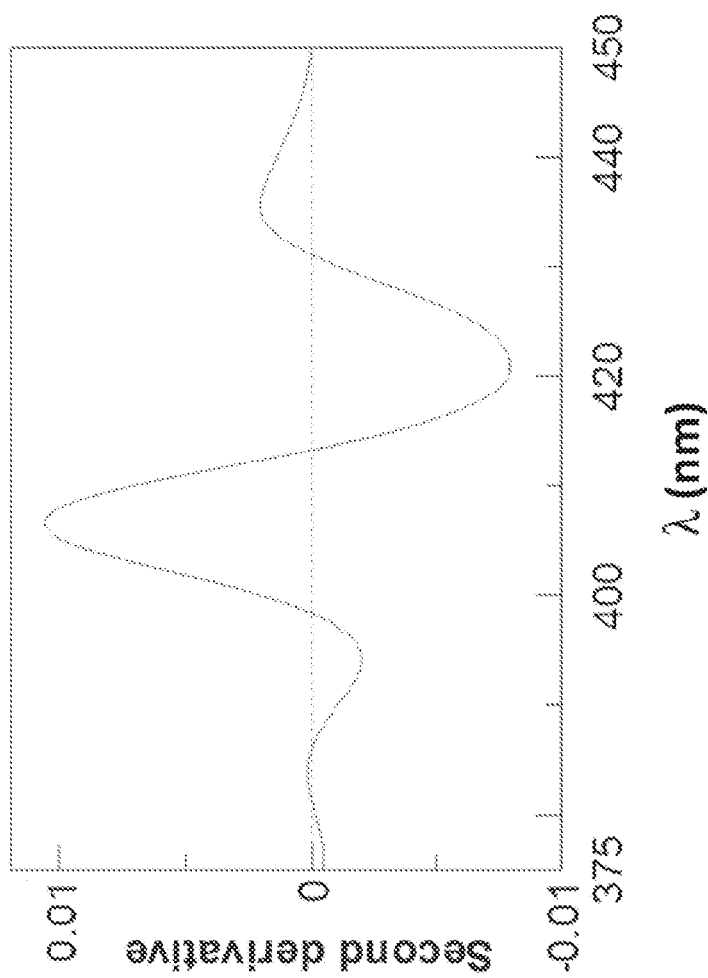
Figure 5E:
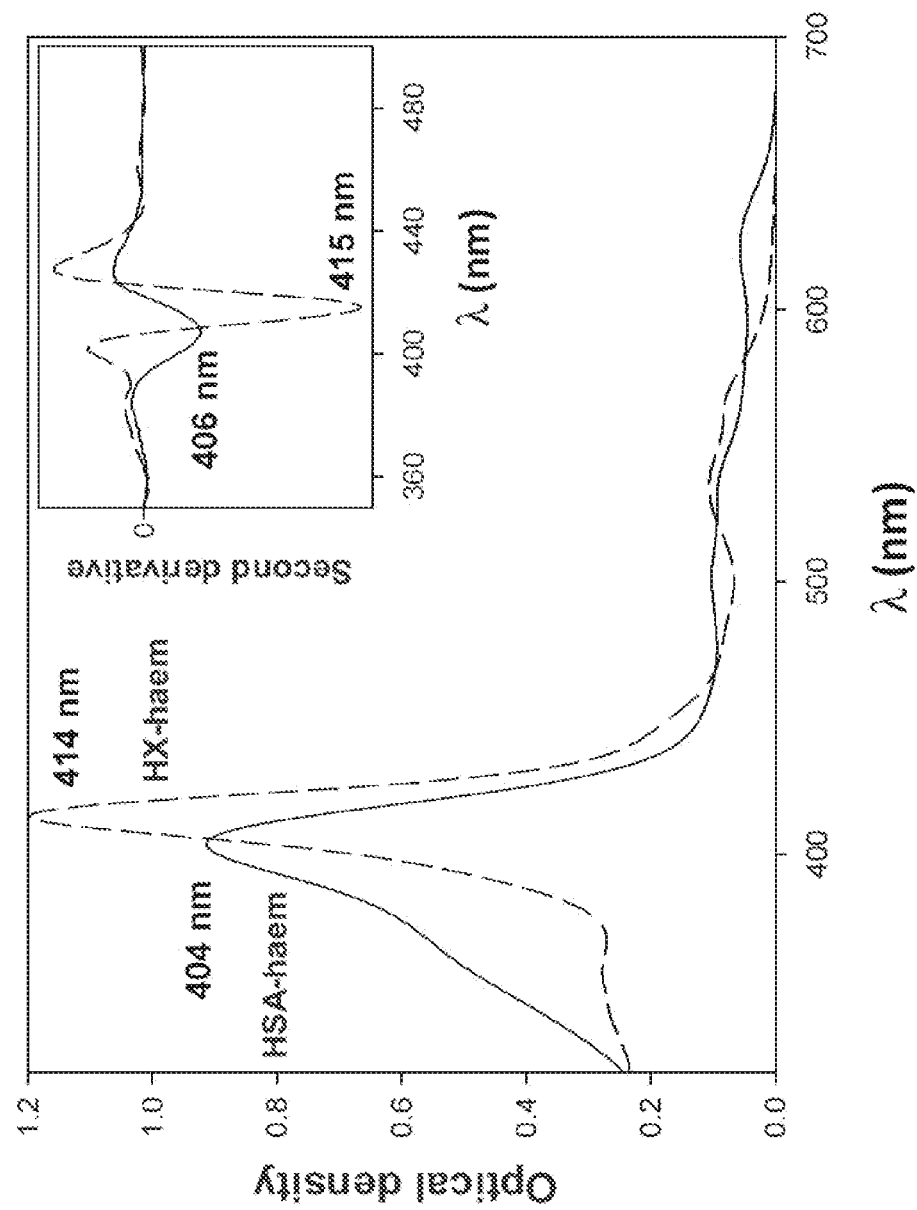

The UV/visible spectra for metHb (dotted line) and metHb-CN (solid line) are presented in FIG. 5c. The experimental conditions were 50 mM potassium phosphate 20 mM NaCl pH 7.4, 25° C. The differential absorption in the Soret band is shown in FIG. 4. FIG. 5d shows the second derivative of this differential spectrum with a maximum at 406 nm and a minimum at 421 nm for the second derivative to be compared with 404 nm/424 nm for the differential spectrum±KCN shown in FIG. 4.

Finally, FIG. 5e shows the comparison of the UV/visible spectra of the two major serum proteins for the binding of haem: HSA and Hx (concentration 10 µM for each). The insert shows their second derivative. The second derivative of Hx is more intense than that of HSA. Thus a small fraction of haem linked to Hx vs HSA will result in a displacement of the second derivative from 406 nm to 415 nm. For example for 10% haem-Hx the minimum is displaced by 406 nm→411 nm and by 25% from 406 nm→414 nm. This confirms the quasi depletion in Hx in the plasmas of patients with pathological haemolysis presented in the examples above.

The invention claimed is:

1. Non-transitory computer readable medium comprising instructions for the execution of the steps of a method of spectral study of a biological fluid when said non-transitory computer readable method is executed by a computer; wherein said method of spectral study of a biological fluid comprises the steps of:
   a) obtaining an absorption spectrum of a sample of the biological fluid;
   b) subtraction from said absorption spectrum of a spectral component associated with oxyhaemoglobin in order to obtain a first intermediate calculated spectrum;
   c) subtraction from said first intermediate calculated spectrum of a spectral component associated with methaemoglobin in order to obtain a second intermediate calculated spectrum;
   d) subtraction from said second intermediate calculated spectrum of a spectral component associated with bilirubin in order to obtain a third intermediate calculated spectrum;
   e) subtraction from said third intermediate calculated spectrum of a spectral component associated with haem linked to serum albumin in order to obtain a fourth intermediate calculated spectrum; and optionally
   f) subtraction from said fourth intermediate calculated spectrum of a spectral component associated with one or more other proteins present in the biological fluid in order to obtain a fifth intermediate calculated spectrum.

2. Non-transitory computer readable medium according to claim 1, in which the spectrum of step a) is obtained in a wavelength domain comprising all or part of the ultraviolet, and/or all or part of the visible range.

3. Non-transitory computer readable medium according to claim 1, in which the spectrum of step a) is obtained from a sample of the diluted biological fluid, so as to obtain a maximum optical density less than or equal to 2.

4. Non-transitory computer readable medium according to claim 1, in which the sample of the biological fluid is buffered at a pH of less than 8.

5. Non-transitory computer readable medium according to claim 1 wherein step b) is carried out by subtracting the spectral component associated with oxyhaemoglobin, obtained by normalization of the first reference spectrum of oxyhaemoglobin, said normalization being carried out with respect to said absorption spectrum by calculating a first normalization coefficient at a wavelength chosen from the group consisting of 416 nanometers, 543 nanometers and 577 nanometers.

6. Non-transitory computer readable medium according to claim 5, in which the first normalization coefficient is calculated by determining the ratio between the values of the second derivatives of the absorption spectrum and of the first reference spectrum at one of the wavelengths.

7. Non-transitory computer readable medium of study according to claim 1, in which the oxyhaemoglobin is at least one of oxyhaemoglobin A and oxyhaemoglobin F.

8. Non-transitory computer readable medium according to claim 1, in which the spectral component associated with methaemoglobin is obtained from at least one spectrum, the at least one spectrum being chosen from among the absorption spectrum, an absorption spectrum of the sample in the presence KCN, a reference spectrum of methaemoglobin, and a reference spectrum of methaemoglobin in the presence of KCN.

9. Non-transitory computer readable medium according to claim 8, in which step c) is carried out by subtracting the spectral component associated with methaemoglobin, obtained by normalization of a second reference spectrum of methaemoglobin, said normalization being carried out by ratio to said first intermediate calculated spectrum by calculating a second normalization coefficient at a wavelength between 350 nanometers and 700 nanometers.

10. Non-transitory computer readable medium according to claim 1, in which step d) is carried out by subtracting the spectral component associated with bilirubin, obtained by normalization of a third reference spectrum SR3 of bilirubin, said normalization being carried out with respect to said second intermediate calculated spectrum by calculating a third normalization coefficient at one or more wavelengths comprising all, or part, of the ultra-violet wavelength range and/or all or part of the visible wavelength range.

11. Non-transitory computer readable medium according to claim 10, in which the third normalization coefficient is calculated by determining the ratio between the values of the second derivatives of the second intermediate calculated spectrum and of the third reference spectrum at one or more wavelengths comprising all, or part, of the ultraviolet wavelength range, and/or all or part of the visible wavelength range.

12. Non-transitory computer readable medium according to claim 1, in which step e) is carried out by subtracting the spectral component associated with haem linked to serum albumin obtained by normalization of a fourth reference spectrum of haem linked to serum albumin, said normalization being carried out with respect to said third intermediate calculated spectrum by calculating a fourth normalization coefficient one or more wavelengths comprising all, or part, of the ultra-violet wavelength range and/or in all, or part, of the visible wavelength range.

13. Non-transitory computer readable medium according to claim 12, wherein the fourth normalization coefficient or the fourth and fifth normalization coefficients K4 and K5 are calculated by determining the ratio between the values of the second derivatives of the third intermediate calculated spectrum and of the fourth reference spectrum one or more wavelengths comprising all, or part, of the ultraviolet wavelength range and/or all, or part, of the visible wavelength range.

14. Non-transitory computer readable medium according to claim 1, wherein the one or more other protein(s) present in the biological fluid is/are one or more of haem linked to haemopexin, carboxylated haemoglobin, a biomarker of haem catabolism by haem oxygenase, myoglobin, porphyrins, degradation products of bilirubin, in urine porphobilin, stercobilin and urobilin.

15. Non-transitory computer readable medium according to claim 1, wherein the method of spectral study of a biological fluid is a for determining a content of at least one protein present in a biological fluid, wherein the method of determination comprises:
   implementing the method as described in claim 1,
   obtaining an oxyhaemoglobin content from the absorption spectrum,
   obtaining a methaemoglobin content from the first intermediate calculated spectrum,
   obtaining a bilirubin content from the second intermediate calculated spectrum, and
   obtaining a haem content linked to serum albumin from the third intermediate calculated spectrum.

16. Non-transitory computer readable medium according to claim 1, wherein the method of spectral study of a biological fluid is a method selected from the group consisting of:
- method for predicting that a subject is at risk of suffering from a disease related to haem or to a haemoprotein, wherein the method comprises at least the steps of:
  - performing the steps of a method for determining at least one protein content in a biological sample of the subject, so as to obtain determined parameters, the method being according to claim 15, and
  - predicting that the subject is at risk of suffering from the disease related to haem or to a haemoprotein on the basis of the determined parameters;
- method for diagnosing a disease related to haem or a haemoprotein in a subject in need thereof, wherein the method comprises at least the steps of:
  - performing the steps of a method for determining at least one protein content in a biological sample of the subject, so as to obtain determined protein contents, the method being according to claim 15, and
  - diagnosing the disease related to haem or to a haemoprotein on the basis of the determined protein contents;
- method for defining the stages of a disease related to haem or a haemoprotein in a subject suffering from the disease, wherein the method comprises at least the steps of:
  - performing the steps of a method for determining at least one protein content in a biological sample of the subject, so as to obtain determined protein contents, the method being according to claim 15, and
  - defining the stages of the disease related to haem or to a haemoprotein on the basis of the determined protein contents;
- method for identifying a therapeutic target for preventing and/or treating a disease related to haem or to a haemoprotein, wherein the method comprises at least the steps of:
  - performing the steps of a method for determining at least one protein content in a biological sample of a first subject, so as to obtain a first determined protein contents, the determination method being according to claim 15, wherein the first subject is suffering from the disease related to haem or to a haemoprotein,
  - performing the steps of the method for determining at least one protein contents in a biological sample of a second subject, so as to obtain a second determined protein content, the method of determination being according to claim 15, wherein the second subject is not suffering from the disease related to haem or to a haemoprotein,
  - selecting a therapeutic target based on the comparison of the first and second determined protein contents;
- method for identifying a biomarker, wherein the biomarker is a diagnostic biomarker of a disease related to haem or to a haemoprotein, a biomarker of susceptibility to a disease related to haem or to a haemoprotein, a prognostic biomarker of a disease related to haem or haemoprotein, or a predictive biomarker in response to treatment of a disease related to haem or a haemoprotein, wherein the method comprises at least the steps of:
  - implementing the steps of a method for determining at least one protein content in a biological sample from a first subject, so as to obtain a first determined content, the determination method being according to claim 15, wherein the first subject is suffering from the disease related to haem or a haemoprotein,
  - performing the steps of the method for determining at least one protein content in a biological sample of a second subject, so as to obtain a second determined protein content, the determination method being according to claim 15, wherein the second subject is a subject not suffering from the disease related to haem or haemoprotein, and
  - selecting a biomarker on the basis of the comparison of the first and second determined protein contents;
- method for screening a compound that may be useful as a drug, wherein the compound has an effect on a known therapeutic target for preventing and/or treating a disease related to haem or to a haemoprotein, wherein the method comprises at least the steps of:
  - implementing the steps of a method for determining at least one protein content in a biological sample of a first subject, so as to obtain a first determined protein contents, the determination method being according to claim 15, wherein the first subject is suffering from the disease related to haem or a haemoprotein and has received the compound,
  - performing the steps of a method for determining at least one protein content in a biological sample of a second subject, so as to obtain a second determined protein content, the determination method being according to claim 15, wherein the second subject is a subject suffering from the disease related to the haem or a haemoprotein, and has not received the compound, and
  - selecting the compound on the basis of the comparison of the first and second determined protein contents;
- method of predicting that a subject is at risk of suffering from a haem- or haemoprotein-related disease, the method comprising at least the steps of
  - performing the steps of a method of determining at least a one protein content in a biological sample of the subject, in order to obtain determined parameters, the method of determination being according to claim 15, and
  - predicting that the subject is at risk of developing the haem- or haemoprotein-related disease based on the determined parameters;
- method for qualifying or disqualifying medical bags containing a biological sample of the subject, wherein the method comprises at least the steps of:
  - performing the steps of a method for determining at least one protein content in the medical bags, so as to obtain determined protein contents, the determination method being according to claim 15, and
  - qualifying or disqualifying the medical bags on the basis of the determined protein contents;
- method for monitoring a treatment against a disease related to haem or to a haemoprotein in a subject suffering from the disease related to the haem or to a haemoprotein, and who has received the treatment, wherein the method comprises at least the following steps:
  - performing the steps of a method for determining at least one protein contents in a biological sample of the subject, so as to obtain determined protein contents, the method being according to claim 15, and
  - monitoring the determined protein contents following a treatment against the disease related to haem or to a haemoprotein in the subject.

17. Non-transitory computer readable medium according to claim 1, in which step e) is carried out by subtracting a spectral component associated with a linear combination of the haem linked to serum albumin and the haem linked to haemopexin, obtained by normalization of the contribution of two fourth and fifth references spectra of respectively haem linked to serum albumin and haem linked to haemopexin, said normalization being carried out with respect to said third intermediate calculated spectrum by calculating two fourth and fifth normalization coefficients at one or more wavelengths comprising all, or part, of the ultra-violet wavelength range and/or in all, or part, of the visible wavelength range.

18. Non-transitory computer readable medium according to claim 17, wherein the fourth and fifth normalization coefficients are calculated by determining the ratio between the values of the second derivatives of the third intermediate calculated spectrum and of fourth and fifth reference spectra at one or more wavelengths comprising all, or part, of the ultraviolet wavelength range and/or all, or part, of the visible wavelength range.

\* \* \* \* \*